United States Patent
Zhou et al.

(10) Patent No.: US 10,537,431 B2
(45) Date of Patent: Jan. 21, 2020

(54) EXPANDABLE SHEATH WITH ELASTOMERIC CROSS SECTIONAL PORTIONS

(71) Applicant: EDWARDS LIFESCIENCES CORPORATION, Irvine, CA (US)

(72) Inventors: Pu Zhou, Irvine, CA (US); Yong Gao, Irvine, CA (US); Erik Bulman, Lake Forest, CA (US); Baigui Bian, Irvine, CA (US); Yidong M. Zhu, Irvine, CA (US); David D. Williams, Bountiful, UT (US); Timothy A. Geiser, Laguna Niguel, CA (US); Michael G. Valdez, Riverside, CA (US); Sonny Tran, Westminster, CA (US); Richard D. White, Poway, CA (US); Thanh Huy Le, Oceanside, CA (US); Tung T. Le, Irvine, CA (US); Alpana K. Gowdar, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/149,947

(22) Filed: Oct. 2, 2018

(65) Prior Publication Data
US 2019/0029820 A1 Jan. 31, 2019

Related U.S. Application Data

(63) Continuation of application No. 14/880,109, filed on Oct. 9, 2015, and a continuation of application No. 14/880,111, filed on Oct. 9, 2015.
(Continued)

(51) Int. Cl.
*A61F 2/24* (2006.01)
*A61M 25/06* (2006.01)
(Continued)

(52) U.S. Cl.
CPC ....... *A61F 2/2427* (2013.01); *A61M 25/0023* (2013.01); *A61M 25/0052* (2013.01);
(Continued)

(58) Field of Classification Search
CPC ... A61F 2/962; A61F 2/2427; A61M 25/0054; A61M 25/01; A61M 2025/0024
See application file for complete search history.

(56) References Cited

U.S. PATENT DOCUMENTS

| 4,601,713 A | 7/1986 | Fuqua |
| 4,710,181 A | 12/1987 | Fuqua |
| (Continued) | | |

FOREIGN PATENT DOCUMENTS

| EP | 0103546 | 3/1984 |
| EP | 0592410 | 10/1995 |
| (Continued) | | |

OTHER PUBLICATIONS

510K Premarket Notification, Jun. 22, 2018.
BSX Structural Heart Update 2018.

*Primary Examiner* — Julian W Woo
(74) *Attorney, Agent, or Firm* — Meunier Carlin & Curfman LLC; Joel B. German

(57) ABSTRACT

An expandable introducer sheath for passage of implant delivery catheters, such as catheters for delivery of prosthetic heart valves. The expandable sheath balances the amounts, shapes and positions of various stiff and elastic structures in the sheath to selectively program the expandability and buckling stiffness of the sheath. The expandable sheath can include, for example, an expandable tubular layer that includes alternating stiff and elastic wall portions of a single radial thickness. The combination of stiff and elastic wall portions allow for torque and push strength to advance the expandable sheath while at the same time accommodating temporary expansion. The expandable sheath can also be
(Continued)

reinforced with a tubular layer of braided fibers or a stent structure for additional strength. Other embodiments include selective use of slots or gaps at the distal end of a stiff wall portion to enhance expandability and distribute strain.

12 Claims, 30 Drawing Sheets

Related U.S. Application Data

(60) Provisional application No. 62/145,968, filed on Apr. 10, 2015.

(51) Int. Cl.
    *A61M 25/00*     (2006.01)
    *A61M 25/01*     (2006.01)
    *A61F 2/97*     (2013.01)

(52) U.S. Cl.
    CPC ........ *A61M 25/0054* (2013.01); *A61M 25/01* (2013.01); *A61M 25/0662* (2013.01); *A61F 2/97* (2013.01); *A61F 2250/0018* (2013.01); *A61M 25/0668* (2013.01); *A61M 2025/0024* (2013.01); *A61M 2025/0681* (2013.01)

(56) References Cited

U.S. PATENT DOCUMENTS

| | | | |
|---|---|---|---|
| 4,738,666 A | 4/1988 | Fuqua et al. | |
| 4,921,479 A | 5/1990 | Grayzel | |
| 5,104,388 A | 4/1992 | Quackenbush | |
| 5,201,756 A | 4/1993 | Horzewski et al. | |
| 5,318,588 A | 6/1994 | Horzewski et al. | |
| 5,320,611 A | 6/1994 | Bonutti et al. | |
| 5,501,667 A | 3/1996 | Verduin, Jr. | |
| 5,674,240 A | 10/1997 | Bonutti et al. | |
| 5,810,776 A | 9/1998 | Bacich et al. | |
| 5,817,100 A | 10/1998 | Igaki | |
| 5,997,508 A | 12/1999 | Lunn et al. | |
| 6,080,141 A | 6/2000 | Castro et al. | |
| 6,090,072 A | 7/2000 | Kratoska et al. | |
| 6,090,136 A | 7/2000 | McDonald et al. | |
| 6,190,357 B1 | 2/2001 | Ferrari et al. | |
| 6,312,443 B1* | 11/2001 | Stone ................ | A61B 17/025 606/198 |
| 6,346,092 B1 | 2/2002 | Leschinsky | |
| 6,358,238 B1 | 3/2002 | Sherry | |
| 6,443,979 B1 | 9/2002 | Stalker et al. | |
| 6,494,860 B2 | 12/2002 | Rocamora et al. | |
| 6,632,236 B2 | 10/2003 | Hogendijk | |
| 6,652,492 B1 | 11/2003 | Bell et al. | |
| 6,814,715 B2* | 11/2004 | Bonutti .............. | A61B 17/3439 604/164.03 |
| 6,899,727 B2 | 5/2005 | Armstrong et al. | |
| 7,438,712 B2 | 10/2008 | Chouinard | |
| 7,591,832 B2 | 9/2009 | Eversull et al. | |
| 7,655,016 B2 | 2/2010 | Demarais et al. | |
| 7,665,016 B2 | 2/2010 | Behrens et al. | |
| 7,678,128 B2 | 3/2010 | Boyle et al. | |
| 7,699,864 B2 | 4/2010 | Kick et al. | |
| 7,713,193 B2 | 5/2010 | Nance et al. | |
| 7,722,568 B2 | 5/2010 | Lenker et al. | |
| 7,762,995 B2 | 7/2010 | Eversull et al. | |
| 7,766,820 B2 | 8/2010 | Core | |
| 7,780,692 B2* | 8/2010 | Nance ................ | A61B 17/3417 606/198 |
| 7,785,360 B2 | 8/2010 | Freitag | |
| 7,837,692 B2 | 11/2010 | Mulholland et al. | |
| 7,892,203 B2 | 2/2011 | Lenker et al. | |
| 7,927,309 B2 | 4/2011 | Palm | |
| 7,951,110 B2 | 5/2011 | Bishop et al. | |
| 7,963,952 B2 | 6/2011 | Wright, Jr. et al. | |
| 8,034,072 B2 | 10/2011 | Van Nguyen et al. | |
| 8,048,034 B2 | 11/2011 | Eversull et al. | |
| 8,090,936 B2 | 1/2012 | Fallon et al. | |
| 8,092,481 B2 | 1/2012 | Nance et al. | |
| 8,252,015 B2 | 8/2012 | Leeflang et al. | |
| 8,282,664 B2* | 10/2012 | Nance ................ | A61B 17/3417 606/191 |
| 8,337,518 B2 | 12/2012 | Nance et al. | |
| 8,414,645 B2 | 4/2013 | Dwork et al. | |
| 8,562,559 B2 | 10/2013 | Bishop et al. | |
| 8,562,673 B2 | 10/2013 | Yeung et al. | |
| 8,597,277 B2 | 12/2013 | Lenker et al. | |
| 8,652,203 B2 | 2/2014 | Quadri et al. | |
| 8,668,668 B2 | 3/2014 | Bishop et al. | |
| 8,690,936 B2 | 4/2014 | Nguyen et al. | |
| 8,728,153 B2 | 5/2014 | Bishop et al. | |
| 8,790,387 B2 | 7/2014 | Nguyen et al. | |
| 8,900,191 B2 | 12/2014 | Lenker et al. | |
| 8,900,214 B2 | 12/2014 | Nance et al. | |
| 9,044,577 B2 | 6/2015 | Bishop et al. | |
| 9,192,751 B2 | 11/2015 | Macaulay et al. | |
| 9,192,752 B2 | 11/2015 | Leeflang et al. | |
| 9,241,735 B2 | 1/2016 | Kick et al. | |
| 9,254,374 B2 | 2/2016 | Thorstenson et al. | |
| 9,259,813 B2 | 2/2016 | Heideman et al. | |
| 9,301,840 B2* | 4/2016 | Nguyen .............. | A61F 2/2427 |
| 9,301,841 B2 | 4/2016 | Nguyen et al. | |
| 9,320,508 B2 | 4/2016 | Carroux | |
| 9,387,314 B2 | 7/2016 | Bishop et al. | |
| 9,393,041 B2 | 7/2016 | Barker et al. | |
| 9,440,054 B2 | 9/2016 | Bishop et al. | |
| 9,642,704 B2 | 5/2017 | Tuval et al. | |
| 9,788,944 B2 | 10/2017 | Daly et al. | |
| 9,801,619 B2 | 10/2017 | Lenker et al. | |
| 9,907,931 B2 | 3/2018 | Birmingham et al. | |
| 2002/0032459 A1 | 3/2002 | Horzewski et al. | |
| 2002/0123793 A1 | 9/2002 | Schaldach et al. | |
| 2003/0004537 A1 | 1/2003 | Boyle et al. | |
| 2004/0087968 A1 | 5/2004 | Core et al. | |
| 2004/0122415 A1 | 6/2004 | Johnson | |
| 2005/0080430 A1 | 4/2005 | Wright et al. | |
| 2005/0085842 A1 | 4/2005 | Eversull et al. | |
| 2005/0125021 A1 | 6/2005 | Nance et al. | |
| 2006/0020321 A1 | 1/2006 | Parker | |
| 2006/0135962 A1 | 6/2006 | Kick et al. | |
| 2006/0135981 A1 | 6/2006 | Lenker et al. | |
| 2006/0217755 A1 | 9/2006 | Eversull et al. | |
| 2007/0021768 A1 | 1/2007 | Nance et al. | |
| 2007/0074805 A1 | 4/2007 | Leeflang et al. | |
| 2007/0087148 A1 | 4/2007 | Okushi et al. | |
| 2008/0004521 A1 | 1/2008 | Hundley et al. | |
| 2008/0004571 A1 | 1/2008 | Voss | |
| 2008/0114331 A1 | 5/2008 | Holman et al. | |
| 2008/0243081 A1 | 10/2008 | Nance et al. | |
| 2010/0094209 A1 | 4/2010 | Drasler et al. | |
| 2010/0094392 A1 | 4/2010 | Nguyen et al. | |
| 2010/0198160 A1 | 8/2010 | Voss | |
| 2011/0112567 A1 | 5/2011 | Lenker et al. | |
| 2011/0190697 A1 | 8/2011 | Farnan | |
| 2011/0251681 A1 | 10/2011 | Shipley et al. | |
| 2012/0116439 A1 | 5/2012 | Ho | |
| 2012/0158033 A1 | 6/2012 | Deal et al. | |
| 2012/0323180 A1 | 12/2012 | Chebator et al. | |
| 2013/0281787 A1 | 3/2013 | Avneri et al. | |
| 2013/0090624 A1 | 4/2013 | Munsinger | |
| 2013/0131718 A1 | 5/2013 | Jenson et al. | |
| 2013/0178711 A1 | 7/2013 | Avneri et al. | |
| 2013/0231735 A1 | 9/2013 | Deem et al. | |
| 2014/0121629 A1 | 5/2014 | Macaulay et al. | |
| 2014/0236122 A1 | 8/2014 | Anderson et al. | |
| 2014/0236123 A1 | 8/2014 | Birmingham et al. | |
| 2014/0379067 A1 | 12/2014 | Nguyen et al. | |
| 2015/0182723 A1 | 7/2015 | Leeflang et al. | |
| 2015/0238178 A1 | 8/2015 | Carroux | |
| 2015/0265798 A1 | 9/2015 | Nihonmatsu et al. | |
| 2015/0320971 A1 | 11/2015 | Leeflang et al. | |
| 2016/0074067 A1 | 3/2016 | Furnish et al. | |
| 2016/0135840 A1 | 5/2016 | Kick et al. | |
| 2016/0213882 A1 | 7/2016 | Fitterer et al. | |
| 2016/0296332 A1 | 10/2016 | Zhou et al. | |

(56) References Cited

U.S. PATENT DOCUMENTS

| | | |
|---|---|---|
| 2016/0296730 A1 | 10/2016 | Zhou et al. |
| 2017/0014157 A1 | 1/2017 | Coyle et al. |
| 2017/0072163 A1 | 3/2017 | Lim et al. |
| 2017/0209133 A1 | 7/2017 | Ciulla et al. |
| 2017/0245864 A1 | 8/2017 | Franano et al. |
| 2017/0252062 A1 | 9/2017 | Fitterer et al. |
| 2018/0161064 A1 | 6/2018 | Fitterer et al. |
| 2018/0199960 A1 | 7/2018 | Anderson et al. |
| 2018/0229000 A1 | 8/2018 | Anderson et al. |

FOREIGN PATENT DOCUMENTS

| | | |
|---|---|---|
| EP | 0696447 A2 | 2/1996 |
| EP | 1139889 | 4/2006 |
| EP | 1804860 | 4/2014 |
| EP | 2288403 | 11/2014 |
| EP | 2862590 | 4/2015 |
| EP | 1694398 | 3/2016 |
| EP | 2101661 | 3/2016 |
| EP | 2995268 | 3/2016 |
| EP | 2475417 | 10/2018 |
| JP | 2004500171 A | 1/2004 |
| JP | 2006116249 A | 5/2006 |
| JP | 2012040145 | 3/2012 |
| WO | 2004037333 | 5/2004 |
| WO | 2008147964 | 12/2008 |
| WO | 2009035745 | 3/2009 |
| WO | 2013044942 | 4/2013 |
| WO | 2014140093 | 9/2014 |
| WO | 2014182959 A2 | 11/2014 |
| WO | 2018148488 | 8/2018 |

\* cited by examiner

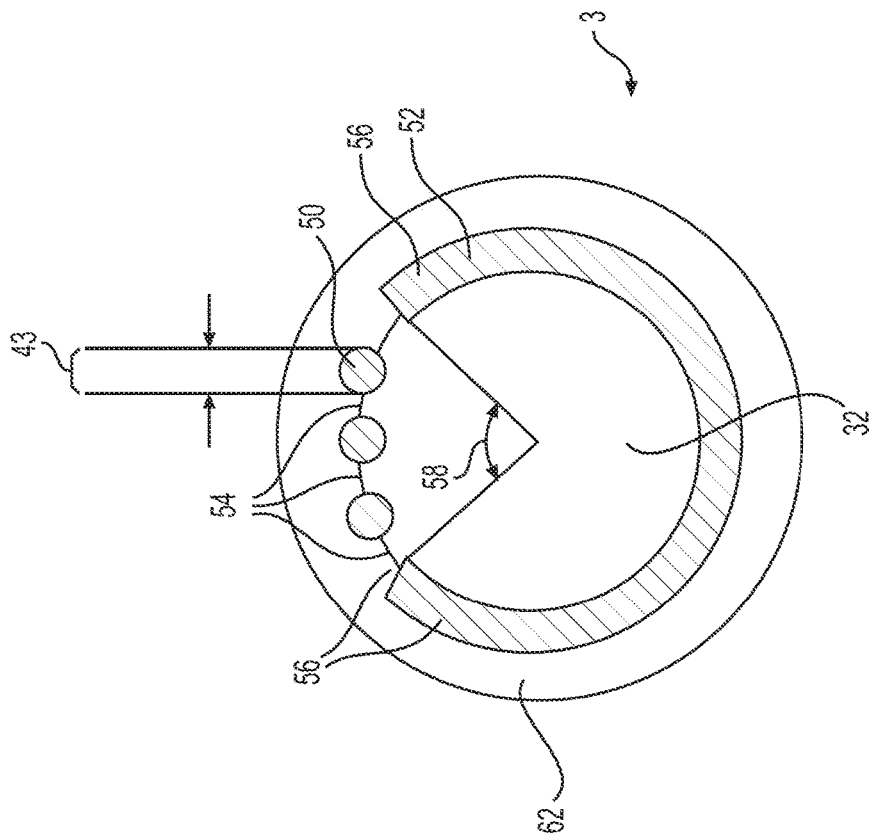
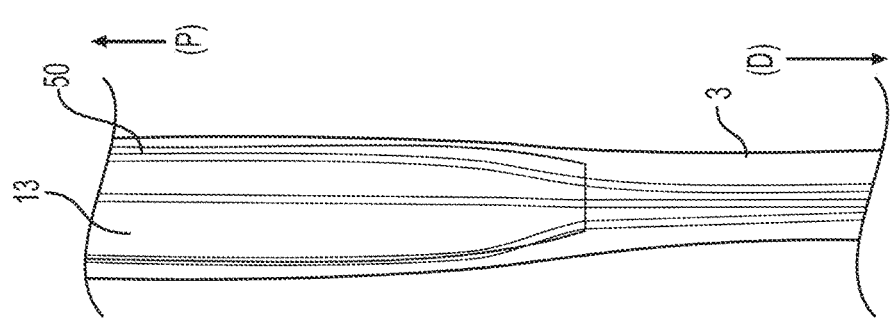

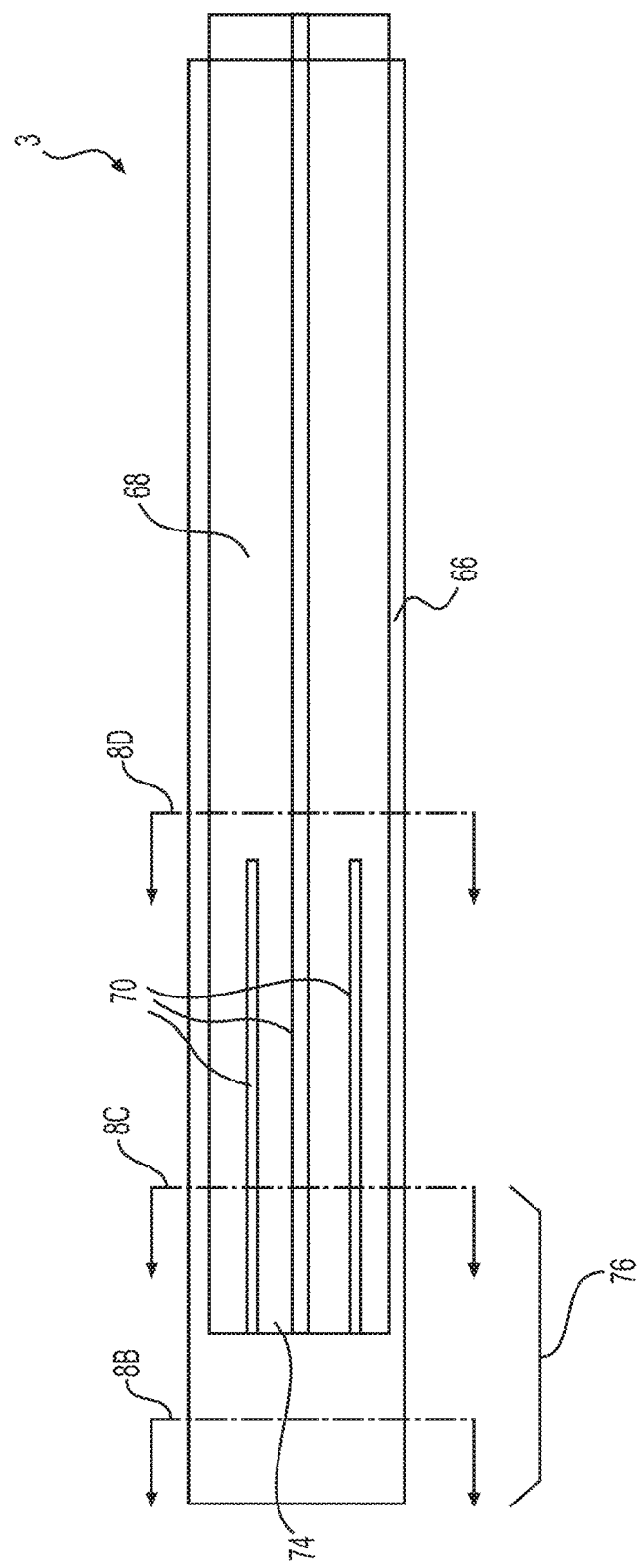

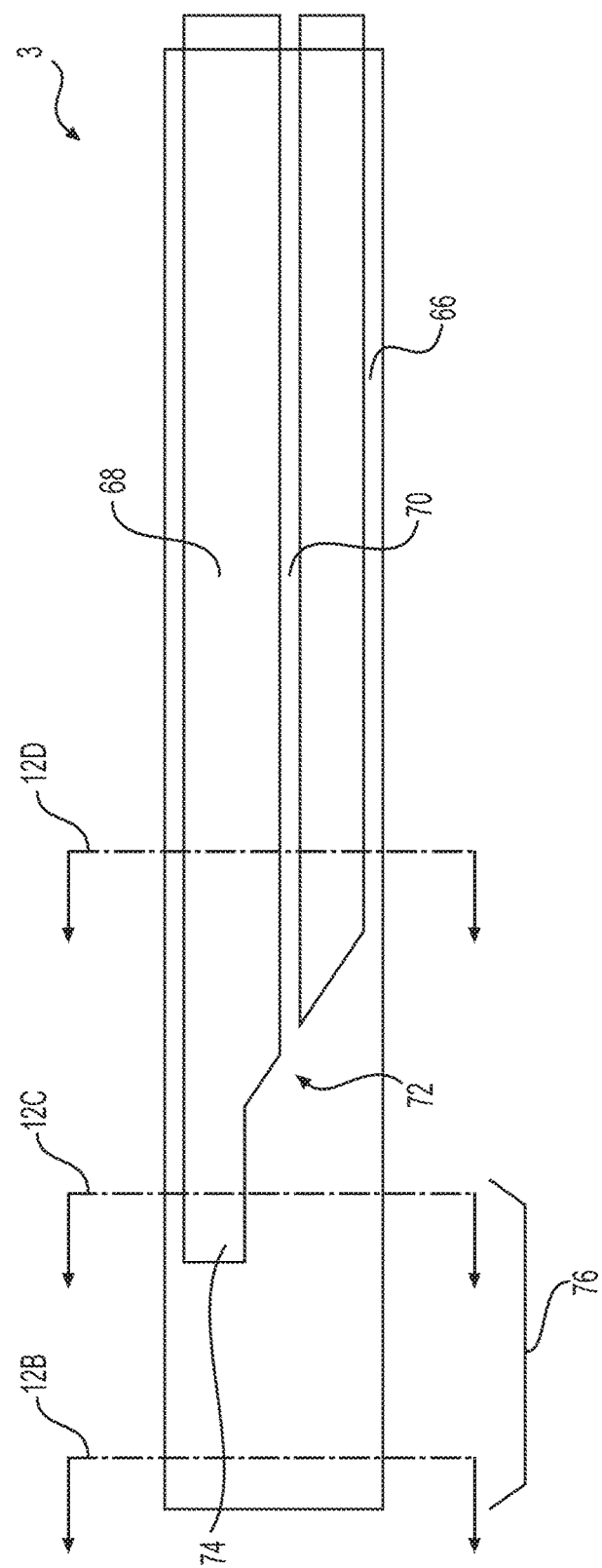

EXPANDABLE SHEATH WITH ELASTOMERIC CROSS SECTIONAL PORTIONS

CROSS REFERENCE TO RELATED APPLICATIONS

This application is a continuation of U.S. application Ser. No. 14/880,111, filed Oct. 9, 2015 and entitled EXPANDABLE SHEATH WITH ELASTOMERIC CROSS SECTIONAL PORTIONS, which claims the benefit of U.S. Provisional Patent Application Ser. No. 62/145,968, filed Apr. 10, 2015 and entitled EXPANDABLE DELIVERY SHEATH. This application is also a continuation of U.S. application Ser. No. 14/880,109, filed Oct. 9, 2015 and entitled EXPANDABLE SHEATH, which claims the benefit of U.S. Provisional Patent Application Ser. No. 62/145,968 filed on Apr. 10, 2015 and entitled EXPANDABLE DELIVERY SHEATH. All of the aforementioned applications are hereby incorporated by reference herein in their entireties and for all purposes.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

U.S. Pat. No. 8,790,387, which is entitled EXPANDABLE SHEATH FOR INTRODUCING AN ENDOVASCULAR DELIVERY DEVICE INTO A BODY and is incorporated herein by reference, discloses a sheath with a split outer polymeric tubular layer and an inner polymeric layer, for example in FIGS. 27A and 28 of '837. A portion of the inner polymeric layer extends through a gap created by the cut and can be compressed between the portions of the outer polymeric tubular layer. Upon expansion of the sheath, portions of the outer polymeric tubular layer have separated from one another, and the inner polymeric layer is expanded to a substantially cylindrical tube. Advantageously, the sheath disclosed in the '387 patent can temporarily expand for passage of implantable devices and then return to its starting diameter.

Despite the disclosure of the '387 patent, there remains a need for further improvements in introducer sheaths for endovascular systems used for implanting valves and other prosthetic devices.

SUMMARY

Disclosed herein is an expandable introducer sheath for passage of implant delivery catheters, such as catheters for delivery of prosthetic heart valves. The expandable sheath can minimize trauma to the vessel by allowing for temporary expansion of a portion of the expandable sheath to accommodate the delivery catheter, followed by a return to the original diameter once the implant passes through. Generally, disclosed herein, are various embodiments balancing the amounts, shapes and positions of various stiff and elastic structures in the sheath to selectively program the expandability and buckling stiffness of the sheath. The expandable sheath can include, for example, an expandable tubular layer that includes alternating stiff and elastic wall portions of a single radial thickness. The combination of stiff and elastic wall portions allow for torque and push strength to advance the expandable sheath while at the same time accommodating temporary expansion. The expandable sheath can also be reinforced with a tubular layer of braided fibers or a stent structure for additional strength. Other embodiments include selective use of slots or gaps at the distal end of a stiff wall portion to enhance expandability and distribute strain.

A sheath of one embodiment includes at least one stiff wall portion and elastic wall portion arranged into an expandable tubular layer. The stiff wall portion has a stiff wall radial thickness and extends generally parallel to and partially around an elongate axis of the sheath and defines at least two edges. The two edges extend generally axially and between an inner surface and outer surface of the stiff wall portion. The stiff wall portion has an elastic wall radial thickness equal to the stiff wall radial thickness and extends generally parallel to and partially around the elongate axis. The elastic wall portion extends between the edges of the stiff wall portion so as to define the expandable tubular layer with a consistent radial thickness at any one cross-section. The expandable tubular layer has a starting profile smaller than the implant and defines a lumen. The expandable layer is configured to temporarily expand at least at the elastic wall portion to allow passage of the implant through the lumen. The expandable layer then returns to its original shape to approximate the starting profile after passage of the implant through the lumen.

In another aspect, the at least one stiff wall portion includes a plurality of stiff wall portions. And, the at least one elastic wall portion includes a plurality of elastic wall portions. The stiff and elastic wall portions can alternate circumferentially around the elongate axis. Also, the sheath can include an elastic outer tubular layer extending around the expandable tubular layer. The sheath can also include an intermediate tubular layer comprising a plurality of braided fibers extending between the expandable tubular layer and the outer tubular layer. The braided tubular fibers can also form an expandable mesh, wherein the elastic outer tubular layer is laminated onto the intermediate tubular layer. The sheath can also include a low friction tubular layer coating the inner surface of the expandable tubular layer. The fibers can extend generally perpendicular to each other to form the expandable mesh.

In another aspect, the two edges of each of the stiff wall portions can extend parallel to the elongate axis. And, the stiff wall portions can be arc segments of the expandable tubular layer.

In another embodiment, the sheath includes a stiff wall portion and an elastic wall portion defining an expandable tubular layer. The stiff wall portion extends generally parallel to and partially around an elongate axis of the sheath and defines at least two edges. The two edges extend generally axially and between an inner and outer surfaces of the stiff wall portion. The elastic wall portion extends generally parallel to and partially around the elongate axis. The elastic wall portion extends between the edges of the stiff wall portion so as to define the expandable tubular layer. The expandable tubular layer has a starting profile smaller than the implant and defines a lumen. And, the expandable tubular layer is configured to temporarily expand at least at the elastic wall portion to allow passage of the implant through the lumen and then return to approximate the starting profile after passage of the implant through the lumen. The elastic wall portion (or portions) can comprise 45 degrees to 90 degrees of an axial cross-section of the expandable tubular layer.

The sheath can also include one or more elongate rods coupled to an inner surface of the elastic wall portion and extending generally parallel to the elongate axis. The stiff wall portion and the elongate rods can have a lubricious inner surface configured to facilitate passage of the implant. The elastic wall portion can also be part of an outer elastic tubular layer and the stiff wall portion can be embedded in the outer elastic tubular layer. The lumen of the expandable tubular layer can be larger where it is defined by the elastic wall portion than where it is defined by the stiff wall portion.

In another aspect, a plurality of elongate rods are coupled to an inner surface of the elastic wall portion and the inner surface of the stiff wall portion. The elongate rods extend generally parallel to the elongate axis and inward into the lumen. The elongate rods can also be spaced circumferentially apart around the lumen of the expandable tubular layer.

In another embodiment, the sheath includes an elastic tubular layer and at least one stiff wall embedded in the elastic tubular layer. A proximal portion of the stiff wall defines at least one first longitudinally extending gap and a distal portion defines at least one second longitudinally extending gap. A cumulative circumferential size of the at least one first longitudinally extending gap is smaller than a cumulative circumferential size of the at least one second longitudinally extending gap. The sheath has a starting profile smaller than the implant and defines a lumen. The sheath is configured to temporarily expand at the at least one first longitudinal gap and the at least one second longitudinal gap to allow passage of the implant through the lumen and then to return to approximate the starting profile after passage of the implant through the lumen.

The second longitudinally extending gap can extent from a distal end of the first longitudinally extending gap.

Also, the sheath can include twice as many second gaps as first gaps. A distal end of each of the first longitudinally extending gaps can extend to a proximal end of a corresponding one of the second longitudinally extending gaps. In another aspect, the sheath can include six second longitudinally extending gaps.

The at least one second longitudinally extending gap can include at least a portion having a progressively, distally increasing cumulative circumferential size.

In another aspect, the sheath includes a plurality of second longitudinal gaps extending linearly and defining a plurality of stiff wall fingers.

DESCRIPTION OF DRAWINGS

FIG. 6A is an enlarged view of a sheath of another embodiment with a capsule passing therethrough;

FIG. 6B is a cross sectional view of the sheath of FIG. 6A;

FIG. 8A is a schematic of another implementation of a delivery sheath with increasing elasticity approaching the distal end region;

FIG. 12A is a schematic of another implementation of a delivery sheath with increasing elasticity approaching the distal end region.

DETAILED DESCRIPTION

Figure 1:
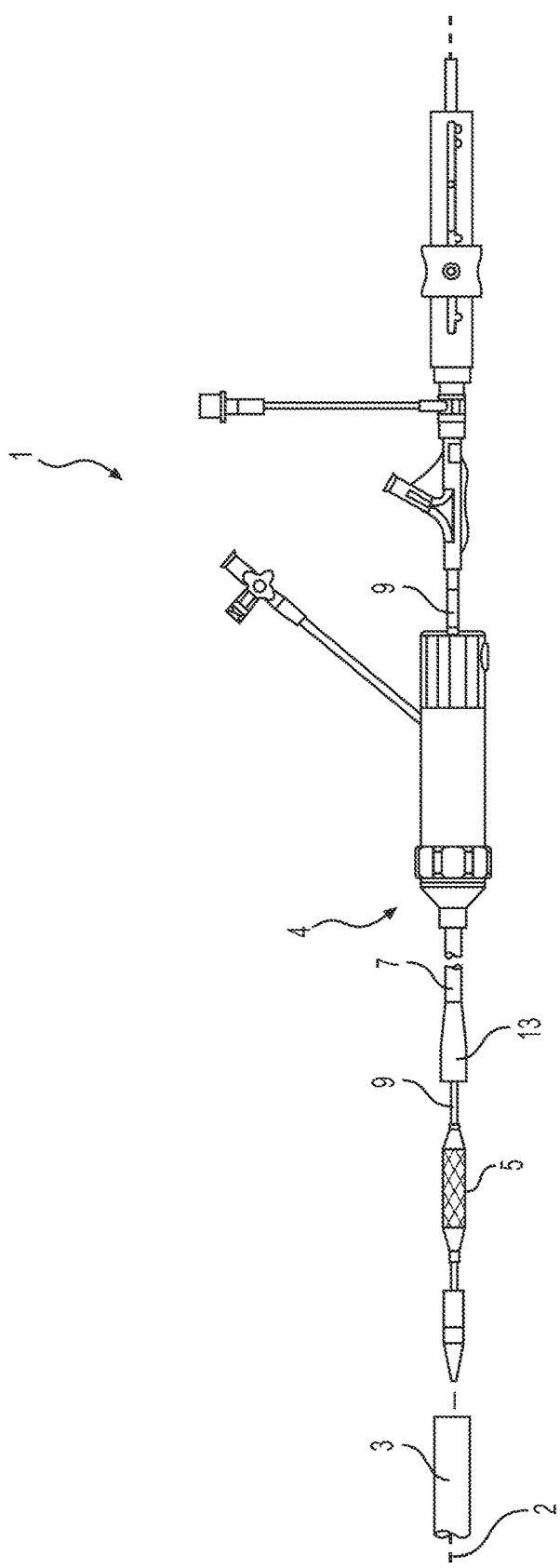
FIG. 1 is an exploded side view of a delivery catheter assembly.
Figure 2:
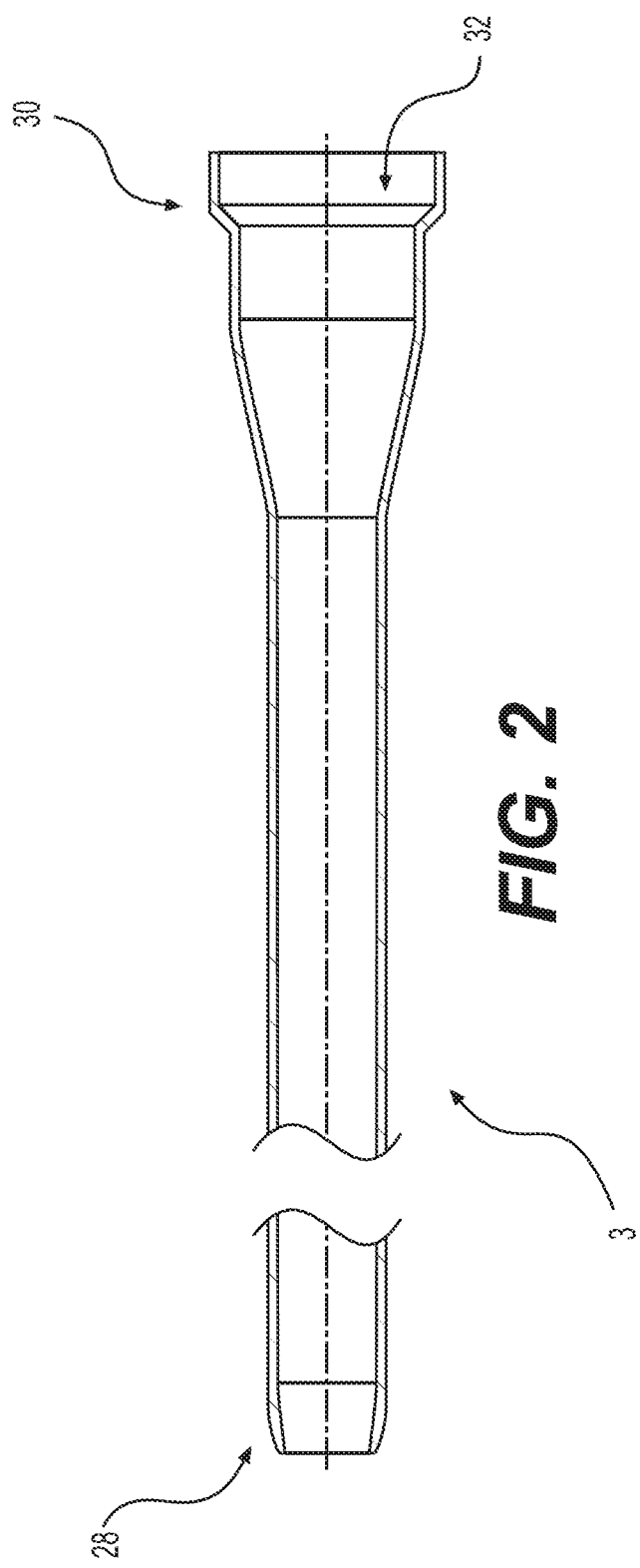
FIG. 2 is a cross-sectional view of a sheath of one embodiment of the present invention.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed herein is an expandable introducer sheath for passage of implant delivery catheters, such as catheters for delivery of prosthetic heart valves. The expandable sheath can minimize trauma to the vessel by allowing for temporary expansion of a portion of the expandable sheath to accommodate the delivery catheter, followed by a return to the original diameter once the implant passes through. Generally, disclosed herein, are various embodiments balancing the amounts, shapes and positions of various stiff and elastic structures in the sheath to selectively program the expandability and buckling stiffness of the sheath. The expandable sheath can include, for example, an expandable tubular layer that includes alternating stiff and elastic wall portions of a single radial thickness. The combination of stiff and elastic wall portions allow for torque and push strength to advance the expandable sheath while at the same time accommodating temporary expansion. The expandable sheath can also be reinforced with a tubular layer of braided fibers or a stent structure for additional strength. Other embodiments include selective use of slots or gaps at the distal end of a stiff wall portion to enhance expandability and distribute strain.

Disclosed herein are elongate delivery sheaths that are particularly suitable for delivery of implants in the form of implantable heart valves, such as balloon-expandable implantable heart valves. Balloon-expandable implantable heart valves are well-known and will not be described in detail here. An example of such an implantable heart valve is described in U.S. Pat. No. 5,411,552, and also in U.S. Patent Application Publication No. 2012/0123529, both of which are hereby incorporated by reference. The elongate delivery sheaths disclosed herein may also be used to deliver other types of implantable devices, such as self-expanding implantable heart valves, stents or filters. The terms "implant" and "implantable" as used herein are broadly defined to mean anything—prosthetic or not—that is delivered to a site within a body. A diagnostic device, for example, may be an implantable.

The term "tube" or "tubular" as used herein is not meant to limit shapes to circular cross-sections. Instead, tube or tubular can refer to any elongate structure with a closed-cross section and lumen extending axially therethrough. A tube can also have some selectively located slits or openings therein—although it still will provide enough of a closed structure to contain other components within its lumen(s).

FIG. 1 illustrates a delivery catheter assembly 1 including an elongate, expandable delivery sheath 3 with a lumen to guide passage of an implant delivery catheter supporting a prosthetic implant 5, such as a prosthetic heart valve. At a proximal end the sheath 3 includes a hemostasis valve that prevents leakage of pressurized blood and a hub 4 for connecting with sheath 3. The delivery catheter assembly 1 can include a steerable guide catheter 7 (also referred to as a flex catheter) and a balloon catheter 9 extending through the guide catheter 7. The delivery catheter assembly 1 can also include a capsule 13 which has an enlarged diameter to hold the implant 5 mounted on the balloon of the balloon catheter 9.

Generally, during use, the sheath 3 is passed through the skin of patient (usually over a guidewire) such that the distal end region of the sheath 3 is inserted into a vessel, such as a femoral artery, and then advanced to a procedure site—such as over the aortic arch to a native aortic heart valve. The nose of the balloon catheter and capsule 13 is inserted through the hemostasis valve at the proximal end of the sheath 3. The steerable guide catheter 7 is used to advance the nose of the balloon catheter 11 and capsule 13 through to and out of the end of the sheath 3. The implant 5 is then advanced out of the capsule 13 and expanded into the native heart valve, such as by balloon inflation or by self-expansion.

The implementations of the delivery sheath shown herein can provide access for other implants and delivery devices needing transient expansion to facilitate passage of the implants or portions of the delivery devices. For example, in some implementations, the delivery sheath can be used to deliver oversized balloon catheters for angioplasty procedures. The term "implant" as used herein need not be a permanent implant—for example the balloon is an implant temporarily—but could be any device delivered into the body for a procedure.

FIGS. 2-5 show one embodiment of sheath 3 including a wall structure having a tip 28 on its distal end and a flared portion on its proximal end 30 and defining a lumen 32 extending therebetween. The wall structure includes an outer elastic layer 20, an intermediate mesh layer 22, a mixed expandable layer 24 and an inner lubricious low-friction liner or layer 26. Generally, the flared proximal end 30 is sized and shaped to accept a distal male end of a hub structure containing, among other things, a hemostasis valve to mediate leakage during insertion of delivery catheters through the lumen 32 of the delivery sheath 3. The sheath 3 can be sized for delivery of prosthetic implants in the form, for example, of stent-mounted soft-tissue heart valves. For such an application, the sheath can have an outside diameter 0.260 inches and an inside diameter of 0.215 inches. Those diameters can vary with the size of the implant and/or the type of implant or other application.

Figure 4:
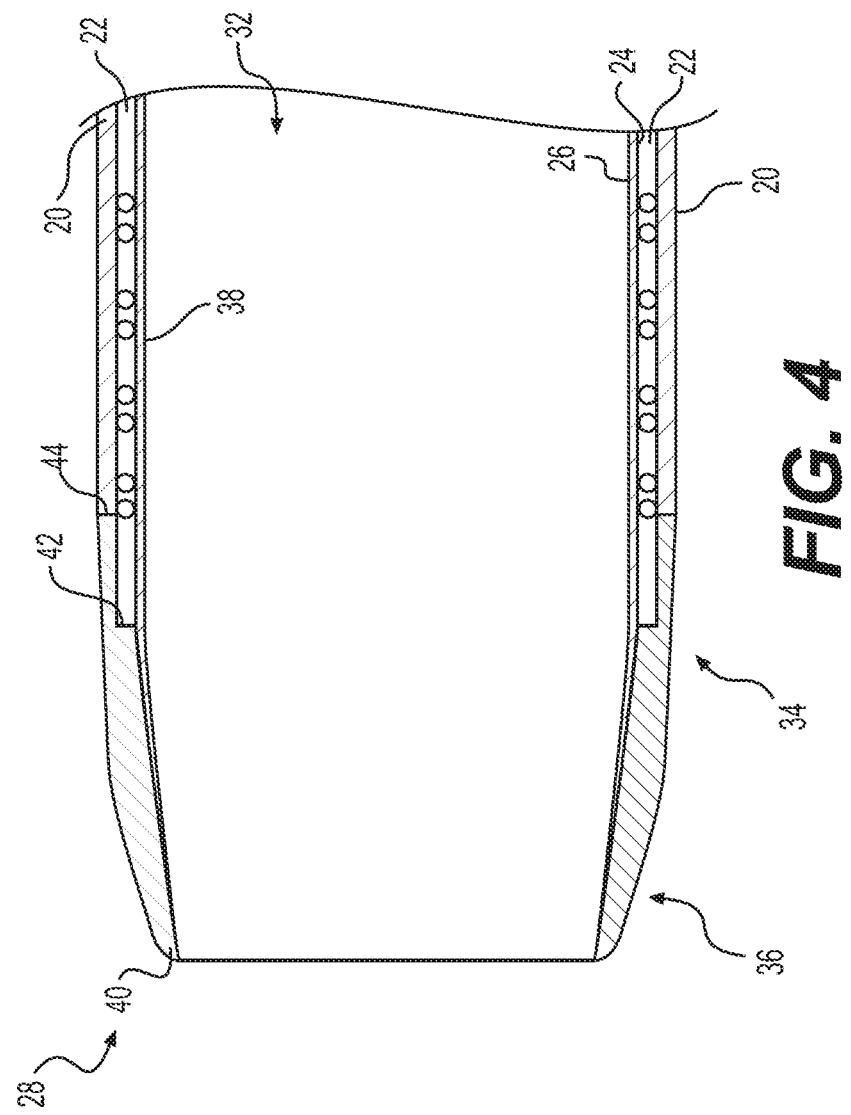
FIG. 4 is an enlarged view of a distal end of the sheath of FIG. 2.

As shown in FIG. 4, the distal tip 28, which has a tapering cylindrical construction, has a proximal taper 34, a distal taper 36, an inner surface 38 and a rounded leading edge 40. The proximal taper 34 has a relatively slight angle with respect to the parallel outer walls of the outer elastic layer 20. Generally, the tip has an outside diameter of about 0.25 inches at the distal end of the proximal taper and an outside diameter of about 0.26 inches at the proximal end of the proximal taper 34. The distal taper 36 has a higher angle increasing to about 20 degrees. The distal taper 36 has a length of approximately 0.060 inches. The leading edge 40 has a rounded radius of about 0.01 inches. The outermost diameter of the leading edge is 0.206 inches and the innermost diameter of 0.187 inches.

The inner surface 38 supports a progressively thinning, distally tapering portion of the mixed expandable layer 24 and inner lubricious layer 26—with the layers getting thinner in the distal direction. Together the inner surface and distally tapering portion of the layers 24, 26 define a distal portion of the lumen 32 through which the implant 5 and capsule 13 can exit.

At its proximal end the distal tip 28 includes an inner annular surface 42 and an outer annular surface 44. The inner annular surface is recessed within the proximal end of the distal tip 28 and the outer annular surface is on the proximal-most edge of the distal tip 28. The inner annular surface 42 is configured to receive and abut a distal edge of the mesh layer 22 and the outer annular surface 44 is configured to abut the distal edge of the outer elastic layer 20.

When assembled to the distal end of the layers 20, 22, 24 and 26 the distal tip 28—which is constructed of a relatively smooth, rigid material—provides support for advancement of the distal end of the sheath 3. The tapers and rounded outer edges minimize trauma when advancing through body lumens. Also, the distal tip 28 helps to maintain the end diameter of the sheath 3 after passage of the implant 5 and capsule 13.

The outer layer 20 has a tubular shape and is preferably constructed of a soft elastomeric material, such as a PEBAX or polyether block amide material, so as to easily expand in response to forces and return to its original dimensions. Also, the elastomeric properties urge the more inner layers to contract back to their original shapes. The outer layer can have an outer diameter of 0.260 inches and is the largest diameter of the layers making up the sheath 3. The outer layer 20 extends around and laminated onto the mesh layer 22 extending through its lumen.

Figure 3:
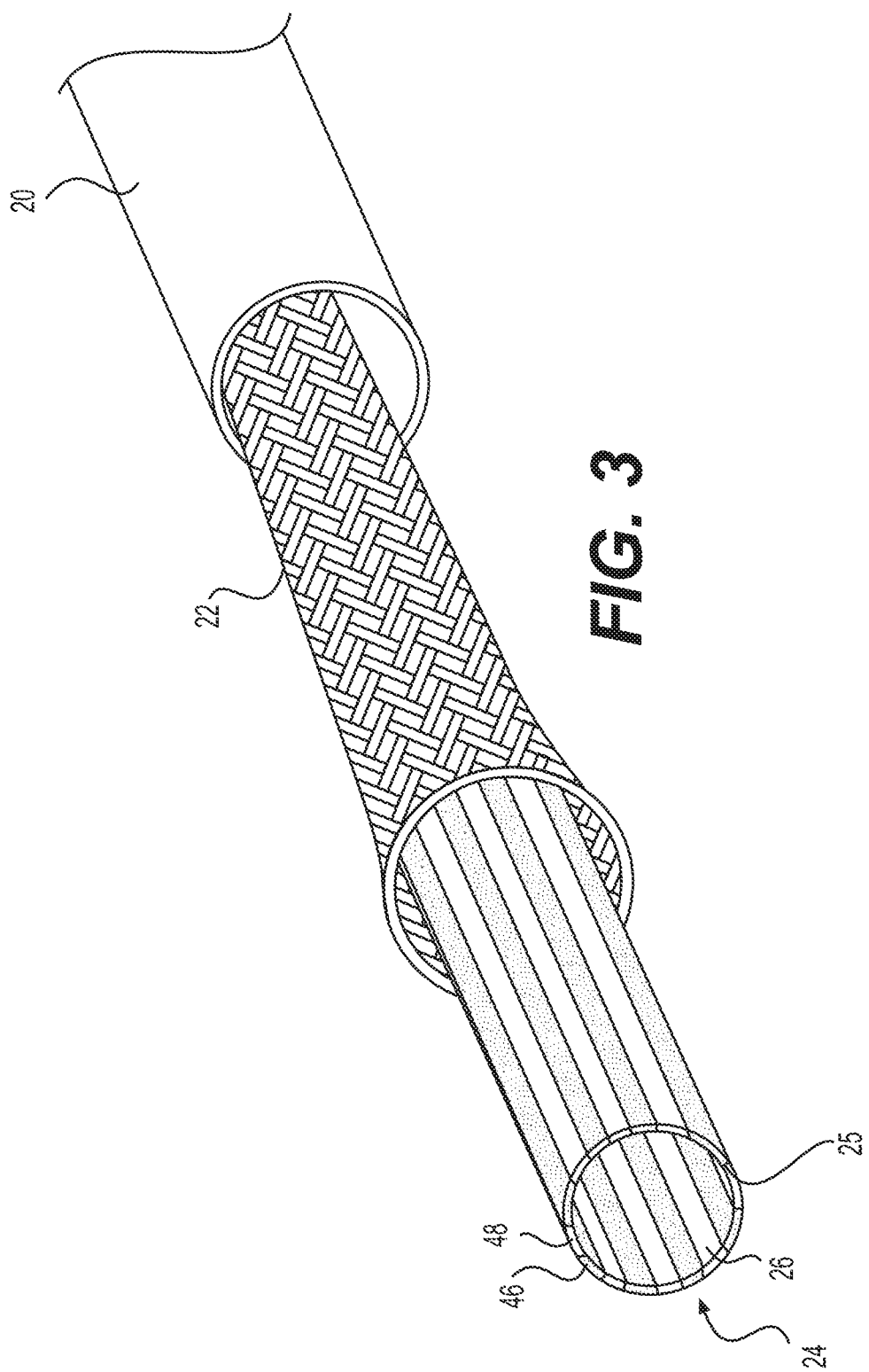
FIG. 3 is a partial exploded view of the sheath of FIG. 2.

The mesh layer 22 is preferably formed of a textile that is comprised of less-elastic components that obtain flexibility and some push stiffness from woven or knit construction. For example, the mesh layer can be constructed of a PET (polyethylene terephthalate) rope or thread material that is woven into a flexible mesh or a sleeve or tube with porous openings to promote expansion and flexibility. The mesh layer 22 can be formed as a plurality of braided fibers. FIG. 3, for example, shows the tubular shape of one embodiment of the mesh layer 22 wherein one group of threads extends perpendicular to another group of threads. Wires or metal could also be used to construct the mesh layer 22, such as woven superelastic nitinol wires with high elastic strain limits.

Figure 5:
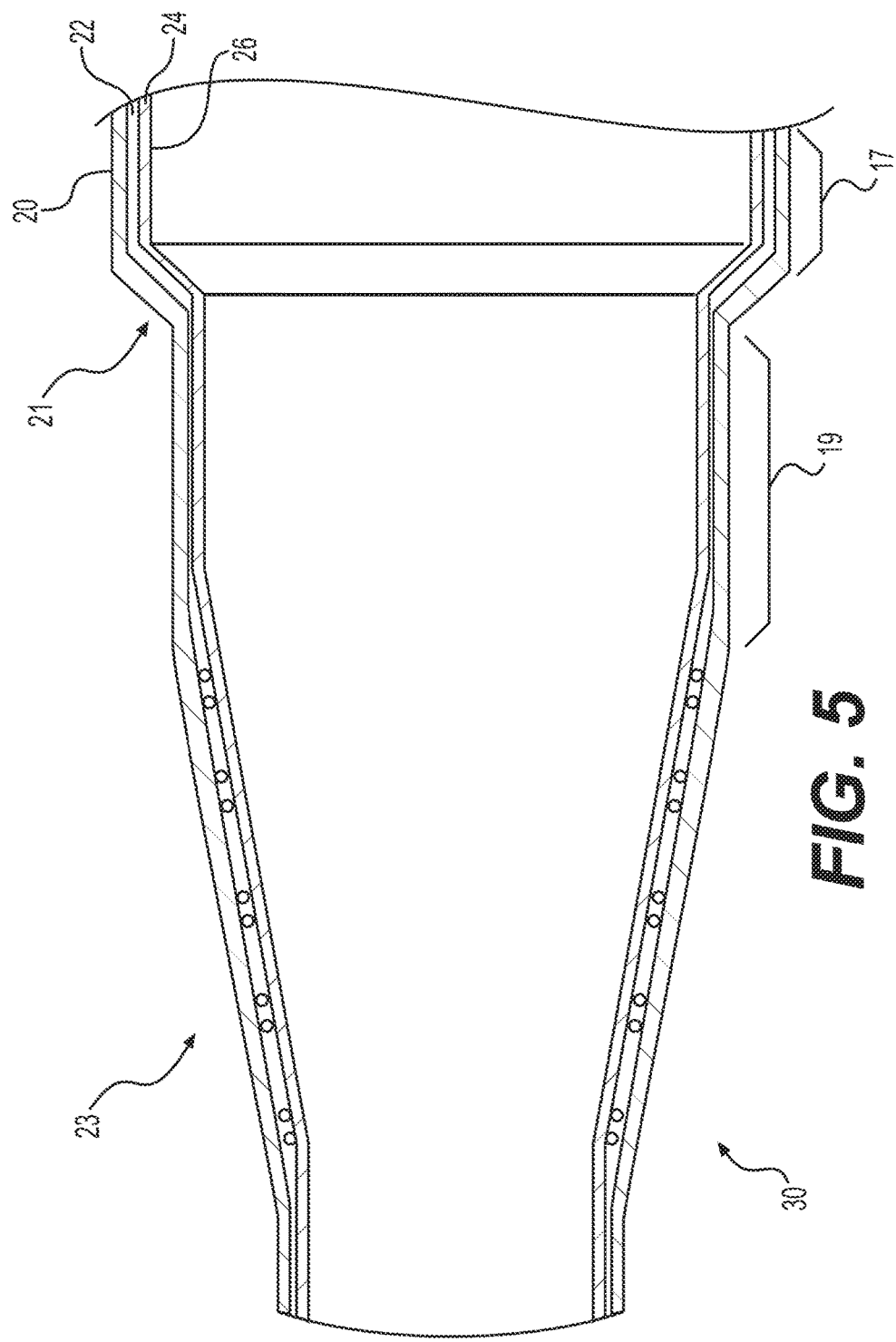
FIG. 5 is an enlarged view of a proximal end of the sheath of FIG. 2.

FIG. 5 shows a cross section of the flared proximal end of sheath 3. Like the distal end, the proximal end includes an outer elastic layer 20, a middle mesh layer 22, a mixed expandable layer 24 and an inner lubricious liner or layer 26. The most proximal region has a first annular portion 17 that is wider than the remainder of sheath 3. The layers 20, 22, 24, and 26 narrow sharply moving distally from the first annular portion of the proximal end 30, forming shoulder 21. The shoulder 21 and first annular portion 17 are configured to connect to the hub 4 of the delivery system 1. Moving distally from the shoulder 21, the layers extend distally to form a second annular portion 19. The walls of the first and second annular portions 17, 19 extend substantially parallel to the longitudinal axis 2 of the sheath 3, and the second annular portion 19 extends a greater distance than the first annular portion 17. Moving distally from the second annular portion 19, the layers 20, 22, 24, and 26 narrow again to form a taper 23. Taper 23 makes a smaller angle with the longitudinal axis 2 than shoulder 21. Taper 23 also extends a greater distance along the longitudinal axis 2 than shoulder 21.

Referring again to FIG. 3, the mixed, expandable layer 24 is constructed of a mixture of alternating full-thickness portions, including soft portions 46 and hard portions 48. The soft portions 46 are constructed of elastomer material—such as materials similar to the outer layer 20—that provide elasticity to the expandable layer 24. The hard portions 48 are constructed of a relatively stiff material and thus provide some columnar stability for advancing the sheath 3 against resistance of a body lumen. The number and spacing of the portions 46, 48 can be adjusted per application. Greater amounts or dimensions of stiff portions 48 can be included for more stiffness. Greater number or dimensions of soft/elastomeric portions 46 can be included for improved expandability and flexibility. TECOFLEX, an aliphatic polyether polyurethane, is one material that can be used for the stiff portions 48.

The portions have a radial thickness from the inside to outside diameter that is equal about the circumference of the layer 24. Also, each of the portions includes a pair of edges 25 between the hard and soft portions that extend between the inner and outer surfaces of the layer 24. The pair of edges can also extend longitudinally, in parallel to the long axis of the sheath 3. The soft/elastomeric portions 46 alternate with the hard portions 48 in arc-segments, their edges in abutting attachment, to form the tubular structure (with a consistent or constant wall thickness) of the mixed expandable layer 24. The hard and soft arc-segments can be equally sized, or they can vary in size.

The inner lubricious layer 26 coats or is adhered on inside surfaces of the expandable layer 24. The layer 26 is preferably a low-friction layer (such as PTFE) and can include a tie-layer attaching the lubricious material to the expandable layer 24. Advantageously, the composite of three layers—including an elastic outer layer, mesh layer and alternating hard/elastomeric layer and inner lubricious liner can provide a good balance of stiffness, expansion/recovery and low resistance to passage of implants.

FIG. 6A shows the delivery sheath 3 of another embodiment of the present invention with the capsule 13 carrying a stent-mounted heart valve or other prosthetic implant 5 passing through the sheath's lumen 32. (For example, the implant can be a 29 mm stent-mounted prosthetic heart valve.) The capsule 13 is passing in a proximal to distal direction. As used herein, "distal" (marked "D" in FIG. 6A), means towards the implantation site, and "proximal" (marked "P" in FIG. 6A) means away from the implantation site. The delivery sheath 3 can comprise a transparent or semi-transparent material through which can be seen the capsule 13. Generally, the sheath of FIGS. 6A and 6B exhibits the ability to temporarily expand for passage of an implant 5 and then return back to its normal diameter afterwards. Also, the sheath 3 can include multiple rods 50, that can be seen through the sheath, and that facilitate lower friction passage of the capsule 13.

FIG. 6B shows a cross section of the delivery sheath 3 including a stiff wall portion 52, an elastic wall portion 54 and the rods 50. The stiff wall portion 52 has a partial circular, or arc-shaped, or C-shaped cross-section with a consistent wall thickness within the cross-section. The C-shape of the stiff wall portion has a pair of edges 56 that extend between the inner and outer surfaces of the stiff wall portion 52. Perpendicular to the cross-section, the two edges extend generally along the length of the stiff wall portion 52 and in the direction of, and parallel to, the elongate axis of the delivery sheath 3.

The elastic wall portion 54 extends between the free edges 56 of the stiff wall portion 52 to define an expandable tubular layer and close the lumen 32 of the sheath 3. As shown in FIG. 6B, the elastic wall portion generally has a shorter arc-length than the stiff wall portion 52 and is positioned further away radially from the axis of the sheath 3 than the inside surface of the stiff wall portion 52. This additional radial clearance provides room for the three rods 50 to extend into the lumen 32. The elastic wall portion 54 can comprise an angle 58 of at least 20 degrees, or as much as 45 to 90 degrees of the cross-section of the sheath 3. The combination and proportions of the elastic and stiff wall portions 54, 52 provide for the temporary expansion and return of the lumen diameter 32 during passage of the implant 5.

The elastic wall portion 54 can be part of an outer elastic tubular layer 62 that externally encapsulates the stiff wall portion 52 in a seamless elastomeric layer. In this manner, the elastic tubular layer 62 helps to seal off the lumen 32 and to urge the C-shaped stiff wall portion 52 back to its original diameter when no longer under pressure from a passing implant. Although the sheath of FIGS. 6A and 6B can have a range of dimensions to suit different applications, the stiff wall portion 52 can, for prosthetic valve delivery purposes, range from 0.002 inches to 0.020 inches in thickness, including about 0.015 inches. The outer portion of the elastic tubular layer 62 adds about another 0.002 inches to 0.020 inches, and in particular about 0.005 inches. In one application, then, the total thickness of the sheath 3 wall can be about 0.020 inches. The unexpanded lumen 32 can have a diameter from 0.050 to 0.250 inches, such as 0.156 inches.

FIG. 6B shows three of the rods 50 embedded into the elastic wall portion 54 and extending into the lumen 32 of the sheath 3. The rods 50 are elongate structures with extruded cross sections—such as a cylindrical shape with a circular cross-section—that extend along the longitudinal axis of the sheath 3. The rods 50 of FIG. 6B are equally spaced from each other in a circumferential direction between the edges 56 of the C-shaped stiff wall portion 52.

Advantageously, the spacing of the rods 50 can increase, as shown in FIG. 6A, during passage of the capsule 13 with stretching of the elastic wall portion 54. Thus the rods can provide some additional stiffness and reduce the surface area and friction that would otherwise be present between the elastic wall portion and the passing implant or capsule without much impact on the expandability of the sheath. As can be seen, at least about half of the cross-section of the rods 50 extends into the lumen 32.

The C-shaped stiff wall portion 52 can be comprised of a range of stiff materials, such as a high-density polyethylene or nylon which provides buckle resistance, pushability, torqueability and a relatively stiff body for the sheath 3. The combination of the elastomeric soft portion 46 helps to mediate kinks of the sheath and to bias against the opening tendency of the stiff wall portion 52. A proximal end of the expandable tubular layer including the wall portions 52, 54 and the outer elastic tubular layer 62 can be flared to provide for hub attachment. Also, a tip could be constructed from the same elastomeric material as the wall portion 54. The tip could include radiopaque properties and be heat fused to the outer tubular layer 62. Manufacture is fairly easy since the components of the sheath 3 can be co-extruded in a single operation.

Figure 7:
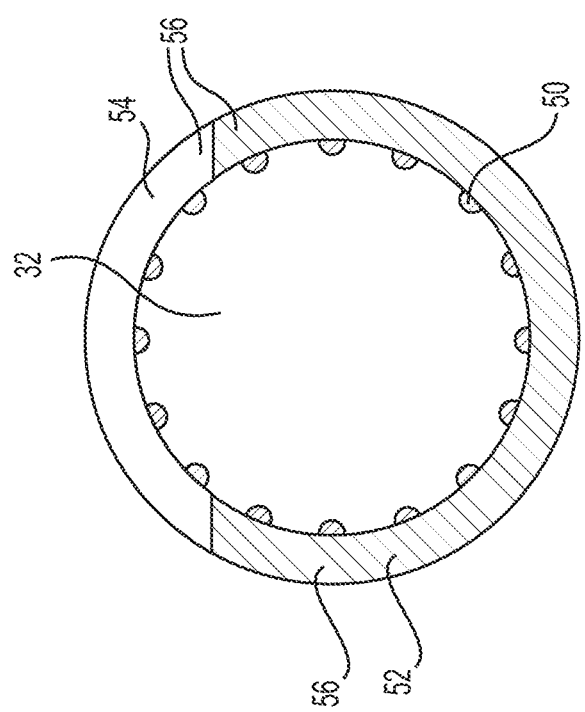
FIG. 7 is a cross sectional view of a sheath of another embodiment.

FIG. 7 shows another embodiment of sheath 3 including wall portions 52, 54 and rods 50 similar to the sheath 3 in FIGS. 6A and 6B. In this embodiment, however, the edges 56 of the stiff wall portion 52 are oriented to be within a common plane. The elastic wall portion 54 also has a thickness matched to the stiff wall portion 52, as opposed to having the encapsulating outer elastic tubular layer 62. The elastic wall portion 54 also takes up a larger angle 58 than the embodiment shown in FIGS. 6A and 6B.

The sheath 3 also includes a larger number of rods 50 which are equally spaced circumferentially about the entire lumen 32. The rods 50 are connected to the inside surfaces of both the stiff wall portion 52 and the elastic wall portion 54. The rods 50 have a semi-circular extruded cross-section. The additional rods 50 can further reduce contact area and the associated friction. The rods 50 can be comprised of stiff, relatively lubricious material to further facilitate sliding. The rods 50 on the stiff wall portion 52 can allow reduction of the overall stiffness of the wall portion as the rods help to increase stiffness.

FIGS. 8A-8D show embodiments wherein the sheath 3 includes an elastic tubular layer 66 having covering one or more stiff wall portions 68. The elastic tubular layer 66 can be a seamless outer layer that guards against blood or fluid leakage. The stiff wall portions define one or more gaps 70. Generally, the cumulative circumferential amount of the cross-section taken up by the gaps 70 is proportional to the resistance to expansion of the sheath 3 at that particular longitudinal position. FIGS. 8A-8D, for example, show the cumulative amount of the gaps 70 increasing distally so that the amount of compression exerted on the implant drops in the distal direction. This can be advantageous as the friction and/or other resistance to advancement of the capsule 13 within the sheath can increase with increase in distance of travel—the drop in expansion resistance can offset somewhat the increased push resistance.

Figure 8B:
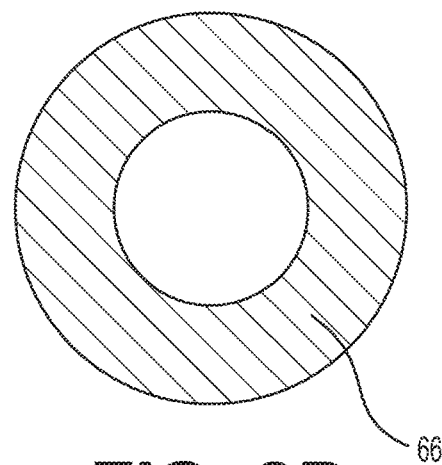
FIGS. 8B-8D are cross sectional schematics of the delivery sheath implementation shown in FIG. 8A.
Figure 8C:
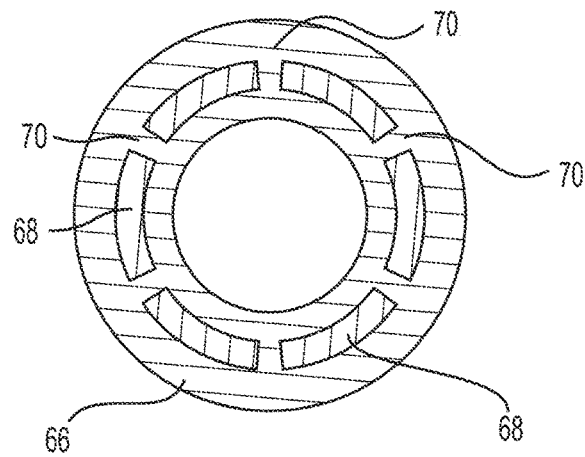
Figure 8D:
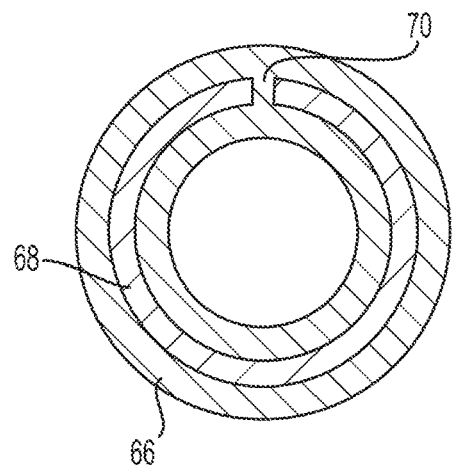

The cross-section shown in FIG. 8D, for example, is taken from a more proximal position and the embedded stiff wall portion 68 takes up significantly more than half of the circumference of the sheath 3. The single gap 70 between ends of the stiff wall portion 68 is about 45 degrees of the circumference forming a C-shaped tube similar to the stiff wall portion 52 described above. Moving distally to the cross-section shown in FIG. 8C shows an additional set of four smaller gaps 70 added to the larger gap. These gaps, as shown in FIG. 8A, tend to define the stiff wall portion 68 into discrete fingers 74. With the increase of the gap size in proportion to the size of the stiff wall portion 68, the expansion stiffness of the sheath 3 drops. The cross-section shown in FIG. 8B is at the distal end and now the stiff wall portion 68 is not present, substantially increasing the expandability of the distal end of the sheath 3.

The gaps 70 can have a range of sizes and positioning, although the gaps shown in FIGS. 8A-8D extend longitudinally and generally parallel to each other. The smaller gaps are circumferentially arranged and spaced from each other and from the larger gap. The multiple gaps 70 with regular spacing facilitate even expansion of elastic tubular layer 66. The full axial length gap can also be of similar circumferential size as the other gaps 70 for a more even distribution of expansion. For example, for six gaps, a 300% strain of a C-shaped tube is divided into 50% at each location. In contrast, tips with a single gap have more localized expansion of the layer 66 and some risk of fracture.

It should be noted that the term 'axial' as used herein is not limited to a straight axis but instead is referring to the general instantaneous direction of a longitudinal structure. In other words, the axis bends with a bend of the elongate structure.

Figure 9A:
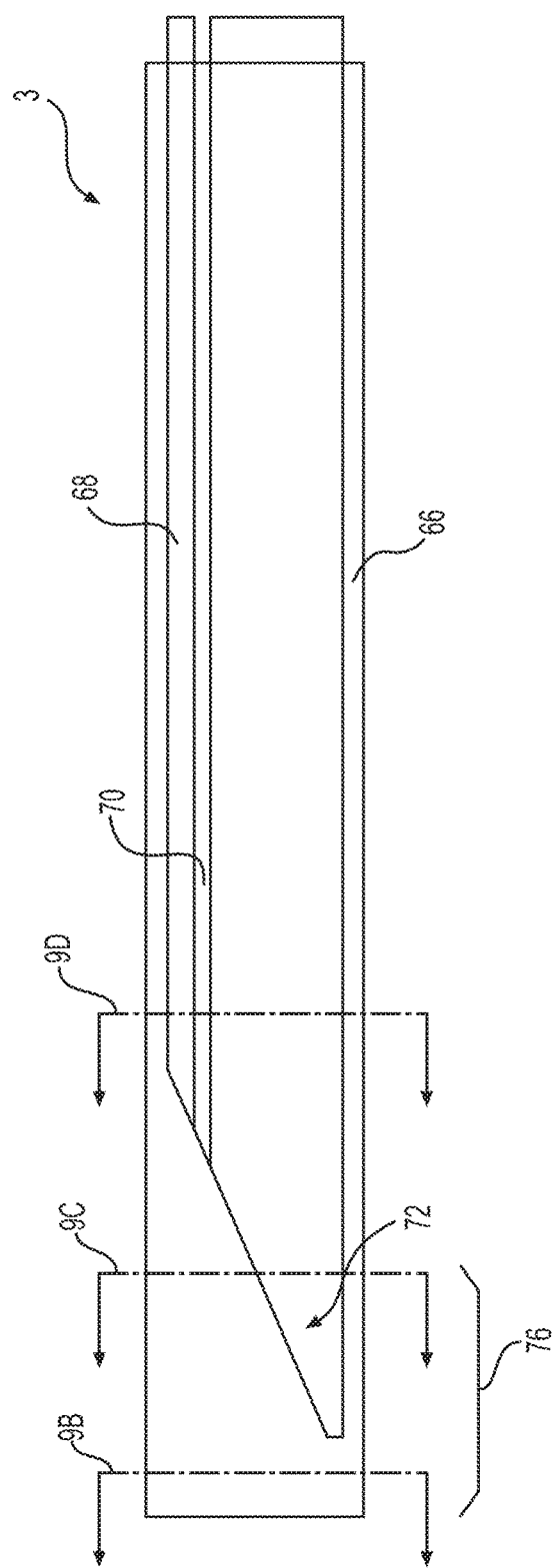
FIG. 9A is a schematic of another implementation of a delivery sheath with increasing elasticity approaching the distal end region.
Figure 9B:
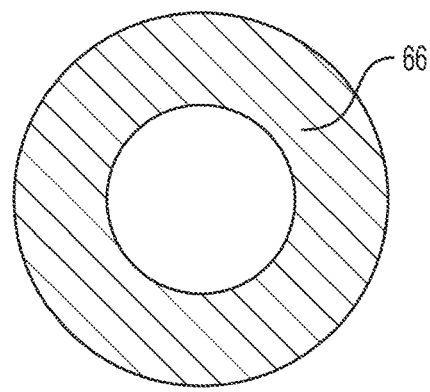
FIGS. 9B-9D are cross sectional schematics of the delivery sheath implementation shown in FIG. 9A.
Figure 9C:
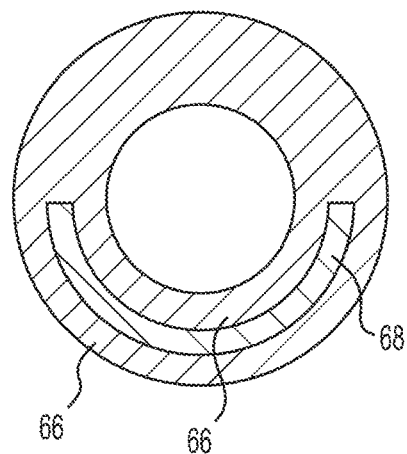
Figure 9D:
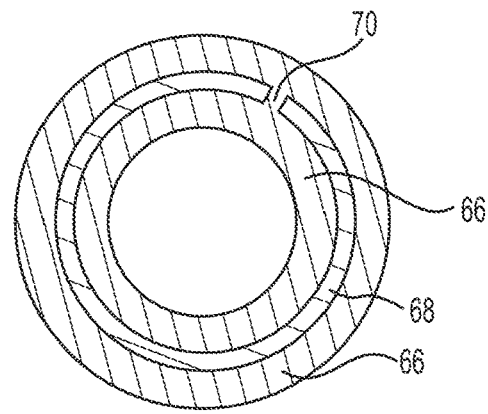
Figure 10A:
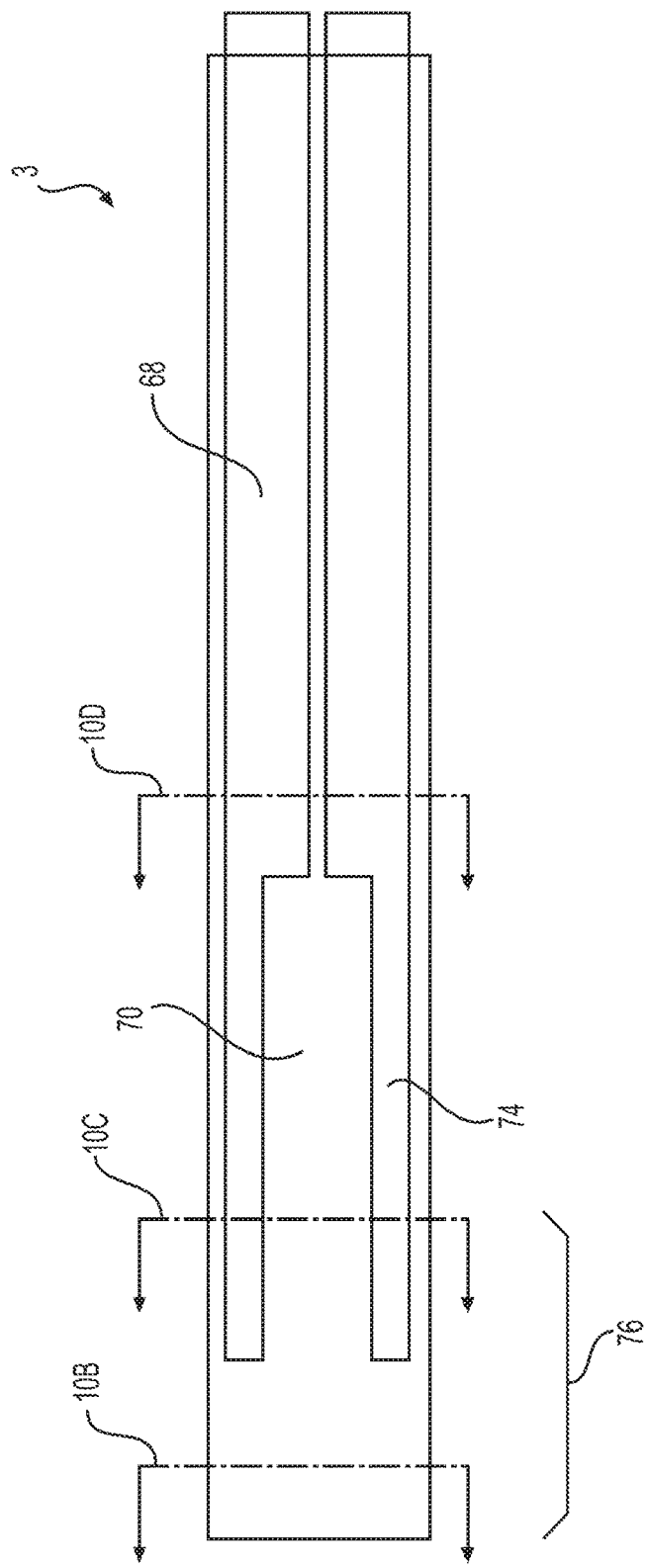
FIG. 10A is a schematic of another implementation of a delivery sheath with increasing elasticity approaching the distal end region.
Figure 10B:
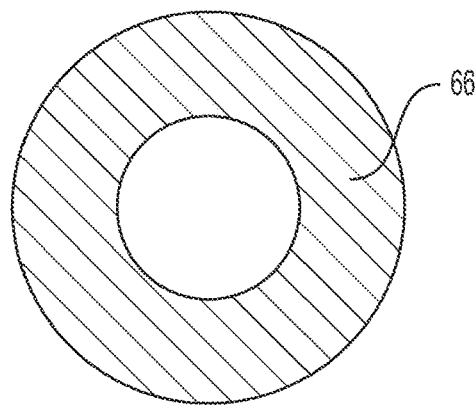
FIGS. 10B-10D are cross sectional schematics of the delivery sheath implementation shown in FIG. 10A.
Figure 10C:
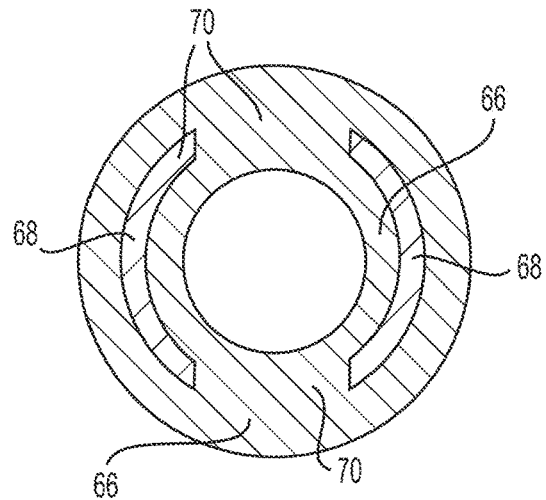
Figure 10D:
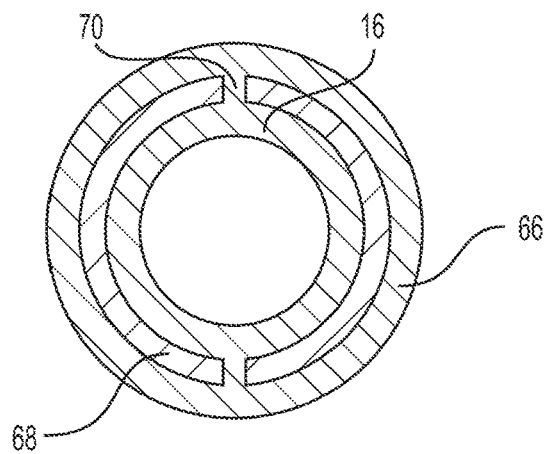
Figure 11A:
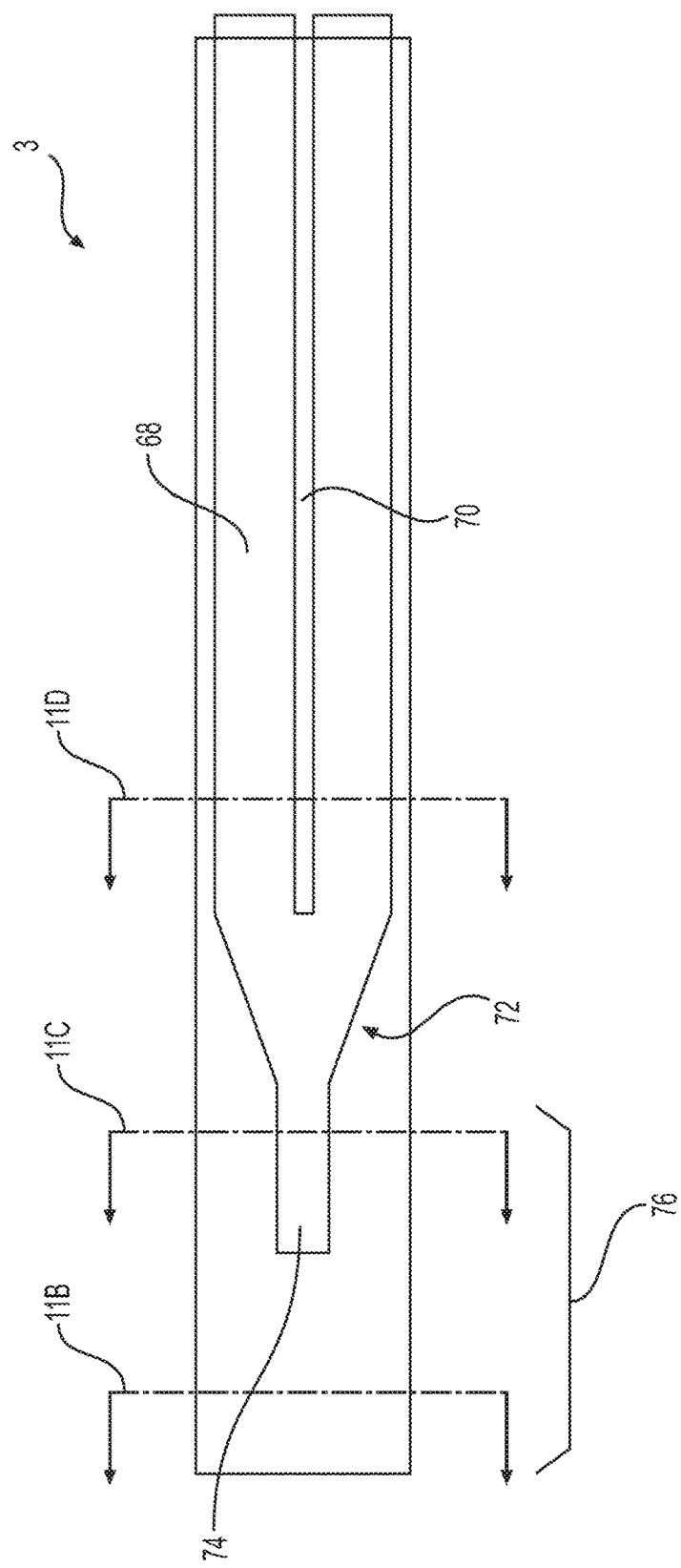
FIG. 11A is a schematic of another implementation of a delivery sheath with increasing elasticity approaching the distal end region.
Figure 11B:
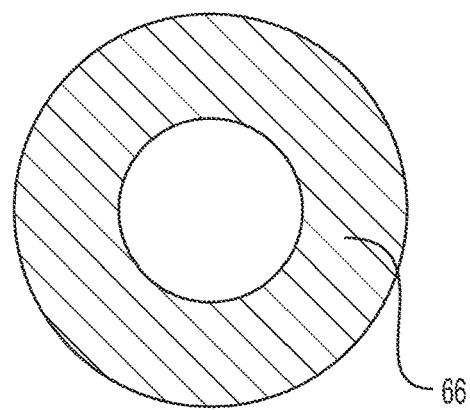
FIGS. 11B-11D are cross sectional schematics of the delivery sheath implementation shown in FIG. 11A.
Figure 11C:
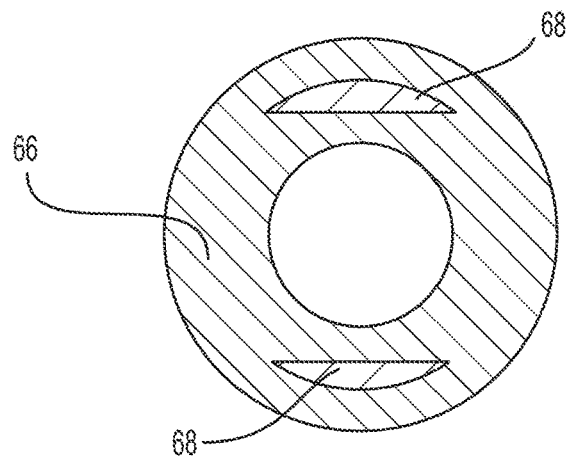
Figure 11D:
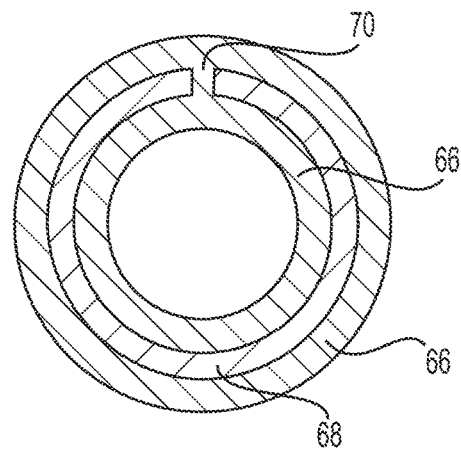
Figure 12B:
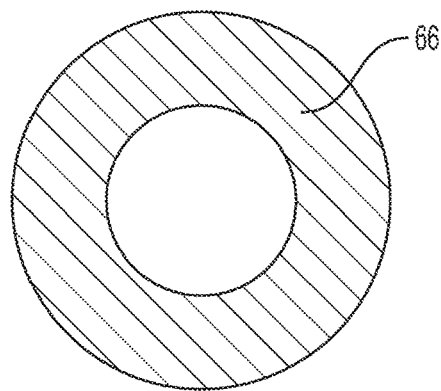
FIGS. 12B-12D are cross sectional schematics of the delivery sheath implementation shown in FIG. 12A.
Figure 12C:
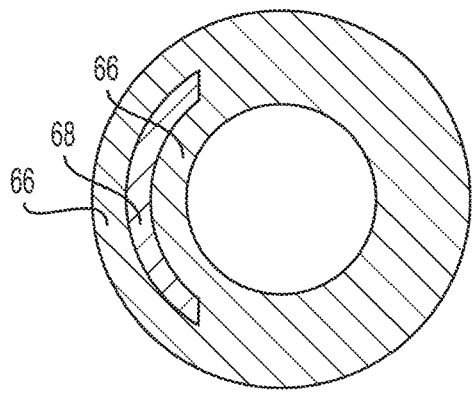
Figure 12D:
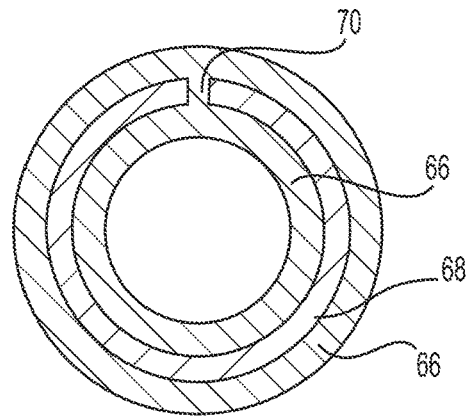

FIGS. 9A-9D show another embodiment wherein the sheath 3 has a single one of the gaps 70 extending longitudinally and then a diagonal cut forming a distal-facing diagonal surface. The diagonal cut serves to progressively decrease the amount of cross-section occupied by the stiff wall portion 68 as it extends in the distal direction, as shown by FIGS. 9D, 9C and 9B.

FIGS. 10A-10D show another embodiment wherein the sheath includes a pair of gaps 70 on opposite sides of the stiff wall portion. The pair of gaps expand in the distal direction, being smallest in diameter at the proximal cross-section of FIG. 10D, making a step increase in size to the cross-section of FIG. 10C. At the final transition, the stiff wall portion 68 disappears for cross-section FIG. 10B. This pattern provides a step decrease in resistance to expansion with each transition in the distal direction.

FIGS. 11A-11D show another embodiment wherein one of the gaps 70 disappears when the stiff wall portion starts a pair of converging diagonal surfaces 72. The diagonal surfaces converge to a single pair of opposing fingers 74. Again, the change in proportion of circumference occupied by the stiff wall portion 68 and gaps 70 adjusts the resistance to expansion of the distal end of the sheath 3.

FIGS. 12A-12D show a combination of some of the prior concepts, wherein the sheath 3 includes the diagonal surface 72 converging to one finger 74.

In the embodiments of FIGS. 8A-12D, the elastic tubular layer 66 and stiff wall portion can move independently of one another for freer expansion. This can be supplemented with addition of a tip region 76, such as by reflowing a soft expandable tube or coating over the distal end of the cuts defining the gaps 70 in the C-shaped stiff wall portion 68. Adding the tip can soften and contour the tip for easier insertion of the sheath 3 as well as protect and cover the distal end of the stiff wall portion 68. In FIGS. 8A-8D the tip region 76 covers some or all of the longitudinal length of the fingers 74 while the remainder of the stiff wall portion with only the single C-shaped cross-section (e.g., FIG. 8D cross-section) is left independent of the elastic tubular layer 66 for free expansion. In FIGS. 9A-12D, the tip region can start distal of the termination of the single gap defining the C-shaped cross section of FIG. 9D.

Although embodiments of the sheath 3 disclosed herein have particular layer constructions, they can include additional layers extending around the inside or outside of the layers depicted in the figures. For example, in some implementations, an undercut/bard or tie layer can be included to keep the stiff wall portion 68 attached to the elastic tubular layer 66. In some implementations, a lubricious outermost layer can be included. The lubricious outermost layer can include a slip additive to increase outer surface lubricity.

In some implementations, such as the one shown in FIG. 6B, the first and second layer 54, 62 and wall portion 52 (which is another layer) are bound together, for example, due to fabrication methods that include coextrusion, heat bonding, glue, or another fixative material. Coextruded implementations are particularly advantageous as they are simple and inexpensive to manufacture. Coextrusion also reduces delamination of outer circumferential layers from inner circumferential layers. In other implementations, the layers are not fully bound and are at least partially, and possibly fully, rotatable with respect to each other. For rotatable implementations, the circumferential tension experienced when an implant 5 is passing through is distributed around the layers 20, 54 and 66, instead of being localized to particular locations. This reduces the chance of rupturing those outer layers. In some implementations, the layers are bound together over certain lengths of the sheath 3, and rotatable over other lengths of the sheath 3. In some implementations, the first and second circumferential layers are bound together only at the distal end region of the sheath 3. Selectively allowing rotation of some portions of the layers allows for some improved tear resistance while preserving some element of structural stiffness. In some implementations, the proximal end of sheath 3 can be flared to attach to external components of the sheath.

In some implementations, various portions of the illustrated embodiments can be supplemented with the longitudinal rods 50. The rods can extend, either partially or fully, along the length of the inner-most surface defining the lumen 32 of the sheath. The longitudinally extending rods can, for example, be supported by the inner-most surface. Here the term "supported by" can mean that the rod is in contact with or extends through that inner surface. For example, the rod can be adhered to or formed on the inner most surface. In some implementations, the longitudinally extending rods can be fully embedded within the inner-most layer. In other implementations, longitudinally extending rods 50 can be partially embedded within the layer, and partially protruding into the inner lumen of the sheath, such as is shown in FIG. 6B.

The height and width of the longitudinally extending rods 50, and thus the amount of the sheath cross-section devoted to the non-elastomeric portions, can vary along the length of sheath 3. A width 43 of the longitudinally extending rods 50 can be, for example, from 0.001 to 0.05 inches. The rods 50 can be circular, ellipsoidal, polygonal, rectangular, square, or a combination of parts of the afore-listed shapes when viewed from a cross section taken generally perpendicular to an elongate axis 2 of the sheath 3. Rods 50 with curved surfaces that protrude into the lumen, such as circular or ellipsoidal surfaces, have the advantage of reducing the area of contact, and therefore the friction, between the sheath and a passing object. Longitudinally extending rods also minimize dimensional change in the longitudinal direction when the sheath is under tension.

Components described as elastic herein can be constructed of elastomers, such as a highly elastic polymer. In some implementations, the elastomeric portion can include polyether, polyurethane, silicone, thermoplastic elastomers, rubber such as styrene-butadiene rubber, or a copolymer of any of the afore-listed highly elastic polymers. The elastomeric material can have an elongation of around 800%. In some implementations, the elastomeric components can comprise a NEUSOFT polymer. The hardness of the NEUSOFT polymer can be, for example, 63 Shore A. NEUSOFT is a translucent polyether urethane based material with good elasticity, vibration dampening, abrasion and tear resistance. The polyurethanes are chemically resistant to hydrolysis and suitable for overmolding on polyolefins, ABS, PC, Pebax and nylon. The polyuerthane provides a good moisture and oxygen barrier as well as UV stability.

The heightened elasticity of various elastic layers, such as layers 20, 62 and 66, facilitates expansion of the layer from its starting profile to allow for the passage of a prosthetic implant 5 and/or delivery capsule 13. In some implementations, an in particular for passage of a capsule containing a stent-mounted prosthetic implant, the lumen can expand to 0.15-0.4 inches, in a fully expanded state. For example, in one implementation, the original diameter of the lumen is 0.13 inches, expands to 0.34 inches during passage of an implant, and shrinks back to 0.26 inches immediately after passage of the implant and continues to shrink with time until eventually returning back to about 0.13 inches. After the passage of the implant, the lumen collapses back to a narrower diameter due to the elasticity of the elastomeric components.

The non-elastomeric components of embodiments described herein (sometimes particularly described as stiff) are made of a generally stiff material that is less elastic than the elastomeric components. The stiff components lend strength to the sheath 3 to complement the elastic properties contributed by the elastomeric components. The stiffer, non-elastomeric components also contribute to buckle resistance (resistance to failure under pressure), kink resistance (resistance to failure during bending), and torque (or ease of turning the sheath circumferentially within a vessel). The stiff material used to fabricate the stiff components can include high density polyethylene (HDPE), Nylon, polyethylene terephthalate (PET), fluoropolymers (such as polytetrafluoroethylene or PTFE), Polyoxymethylene (POM) or any other suitably stiff polymer. The elongation of the non-elastomeric, stiff components can be, for example, around 5%. The hardness of an HDPE non-elastomeric, stiff component can be, for example, around 70 Shore D.

The non-elastomeric components can also be made of a material that is more lubricious than the elastomeric components, and so as to reduce friction between components and/or the components and the implant 5, capsule 13 or other adjacent contacting objects.

Figure 13:
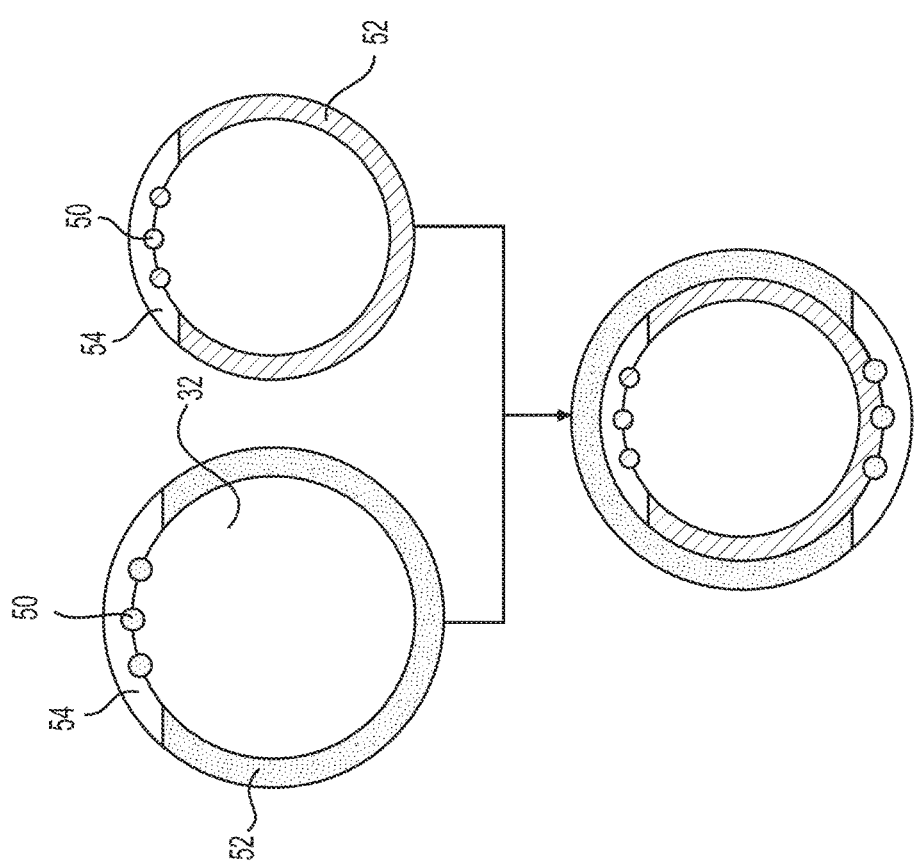
FIG. 13 is a schematic of assembly of two sheaths into a combination sheath of another embodiment of the present invention.

Embodiments disclosed herein can be employed in combinations with each other to create sheaths with varying characteristics. FIG. 13 shows combination of two single-layer tubes nested into each other. Each of the single layer tubes includes a stiff wall portion 52 having a C-shape and an elastic wall portion 54 to close the C-shape around lumen 32. Each single layer tube also includes rods 50 in a similar configuration to the embodiment of FIG. 6B. One of the single layer tubes has a smaller diameter and fits within the lumen 32 of the other tube. The advantage of this combination is a more balanced distribution of elastic wall portions 54 on both sides of the tube which in turns distributes the strains of expansion. The other embodiments disclosed herein can be nested within each other to adjust expansion resistance and distribution.

Figure 14:
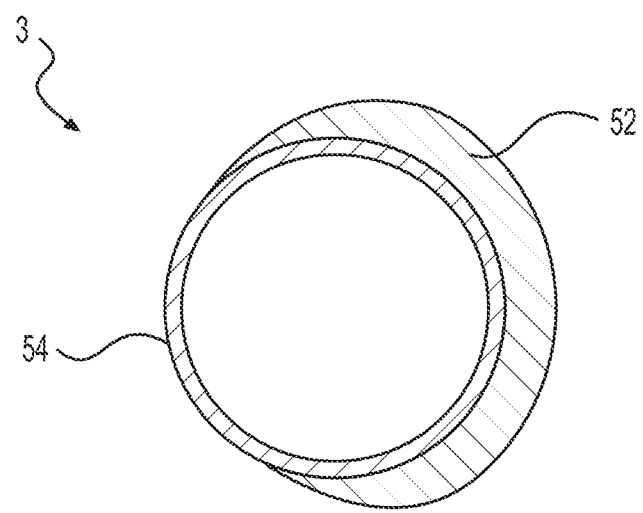
FIGS. 14-16 are cross-sections of embodiments sheaths having expandable thinned wall sections.
Figure 15:
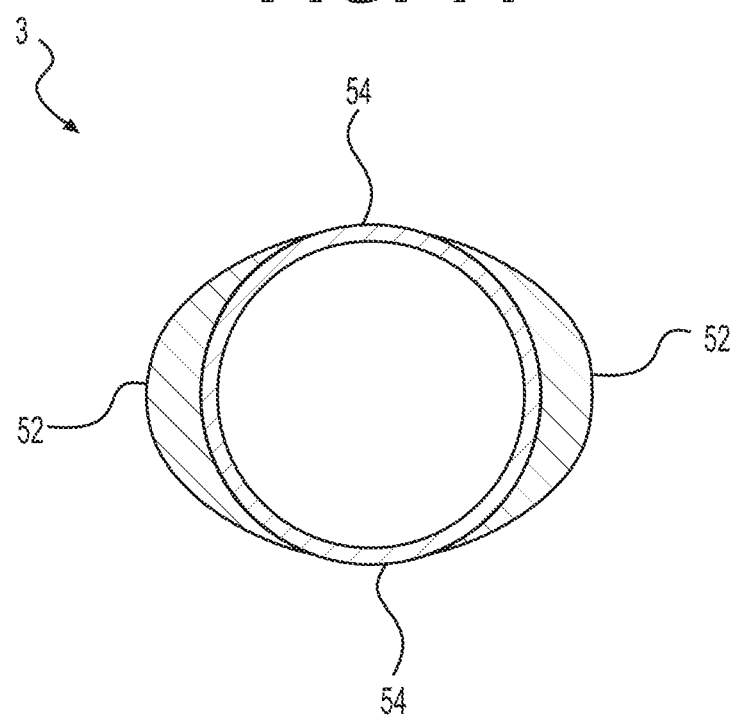
Figure 16:
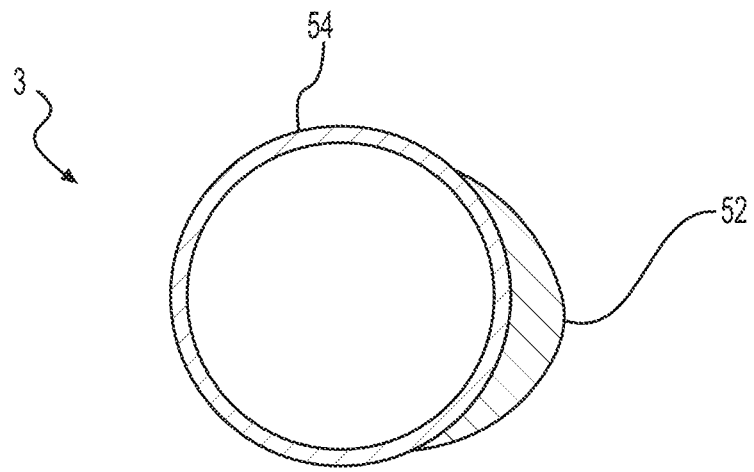

FIGS. 14, 15 and 16 show variations of the sheath 3 that include stiff wall portion 52 and elastic wall portion 54, with the elastic wall portion having a lesser wall thickness for additional flexibility in comparison with the stiff wall portion 52. In these embodiments the wall portions can have the same material with the additional flexibility being due to the reduced thickness. Or the reduced thickness can be combined with more elastomeric material composition.

FIG. 14 shows an embodiment of the sheath 3 with a C-shaped stiff wall portion 52 combined with a thin elastic wall portion 54. FIG. 15 shows the use of two elastic wall portions 54 and two thick, stiffer wall portions 52 on opposing sides, positioning the strain of expansion on opposing sides of the sheath 3. FIG. 16 shows an embodiment of the sheath 3 with more than half or ⅔ or ¾ of the circumference of the sheath being a thinned elastic wall portion 54.

Figure 17:
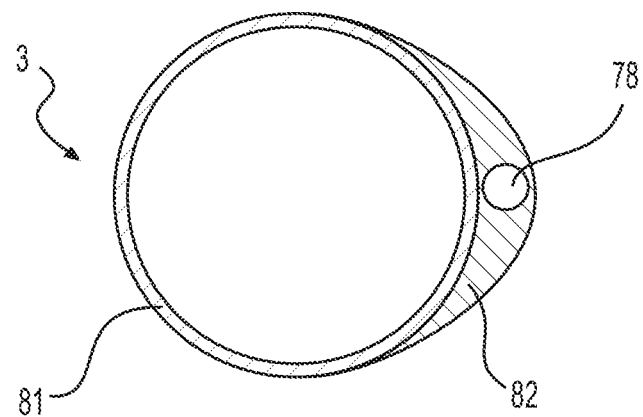
FIGS. 17-19 are cross-sections of embodiments of sheaths having wires or strips reinforcing expandable walled tubes.
Figure 18:
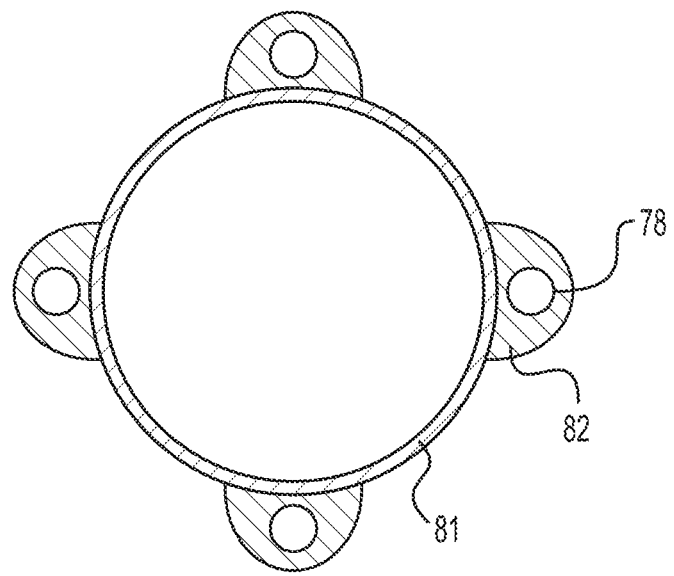
Figure 19:
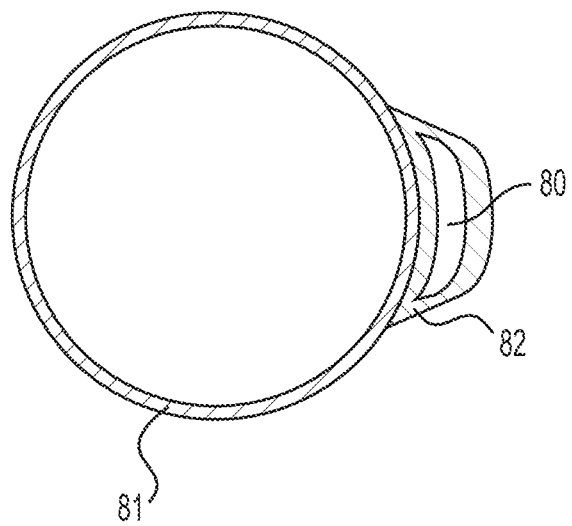

FIGS. 17, 18 and 19 show embodiments wherein wires 78 or strips 80 can be embedded into structures 82 to selectively reinforce an expandable, elastic tubular layer 81. The structures 82 can be thickened mounds or features applied longitudinally—such as be coextrusion—to the outside surface of the elastic tubular layer 81. The wires or strips can be constructed of relatively stiffer materials for selective reinforcement. FIGS. 17 and 18 show the use of wires 78 and, for increased stiffness, FIG. 19 shows the use of a strip 80 embedded in the structure 82.

The sheaths of FIGS. 14-19 can be manufactured as described above, including via reflowing, gluing, bonding, welding, etc. Materials can include HDPE or TECOFLEX for the stiffer components. Other materials herein can also be used for stiff or elastic components. Also, the materials compositions can be varied to include metals, ceramics and other materials than just polymers. Other features can be applied to the embodiments of FIGS. 14-19 including a lubricious liner, hydrophilic or other coatings, silicone or other liquids or printing.

Figure 20:
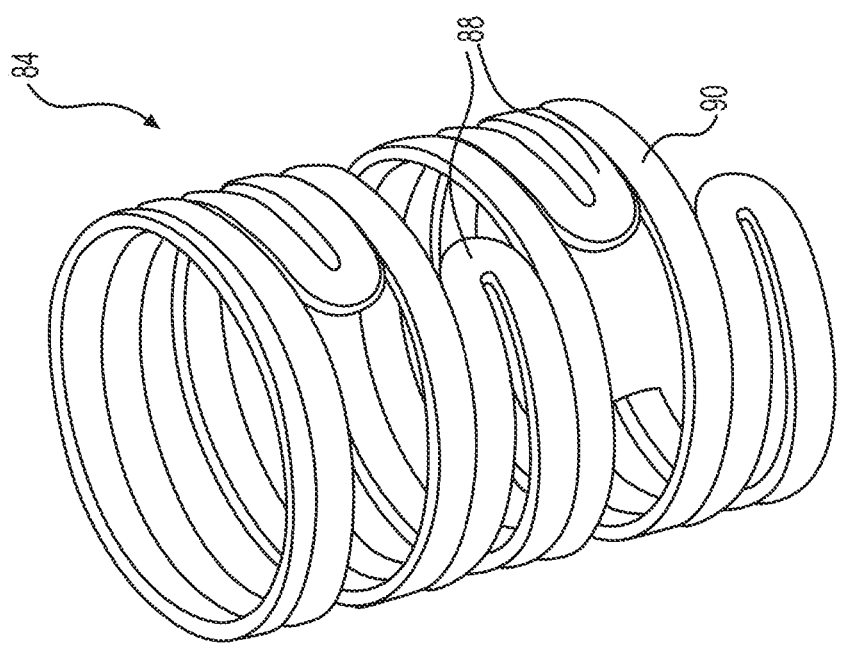
FIG. 20 is a partial perspective view of a stent for an end of a sheath of another embodiment of the present invention.
Figure 21:
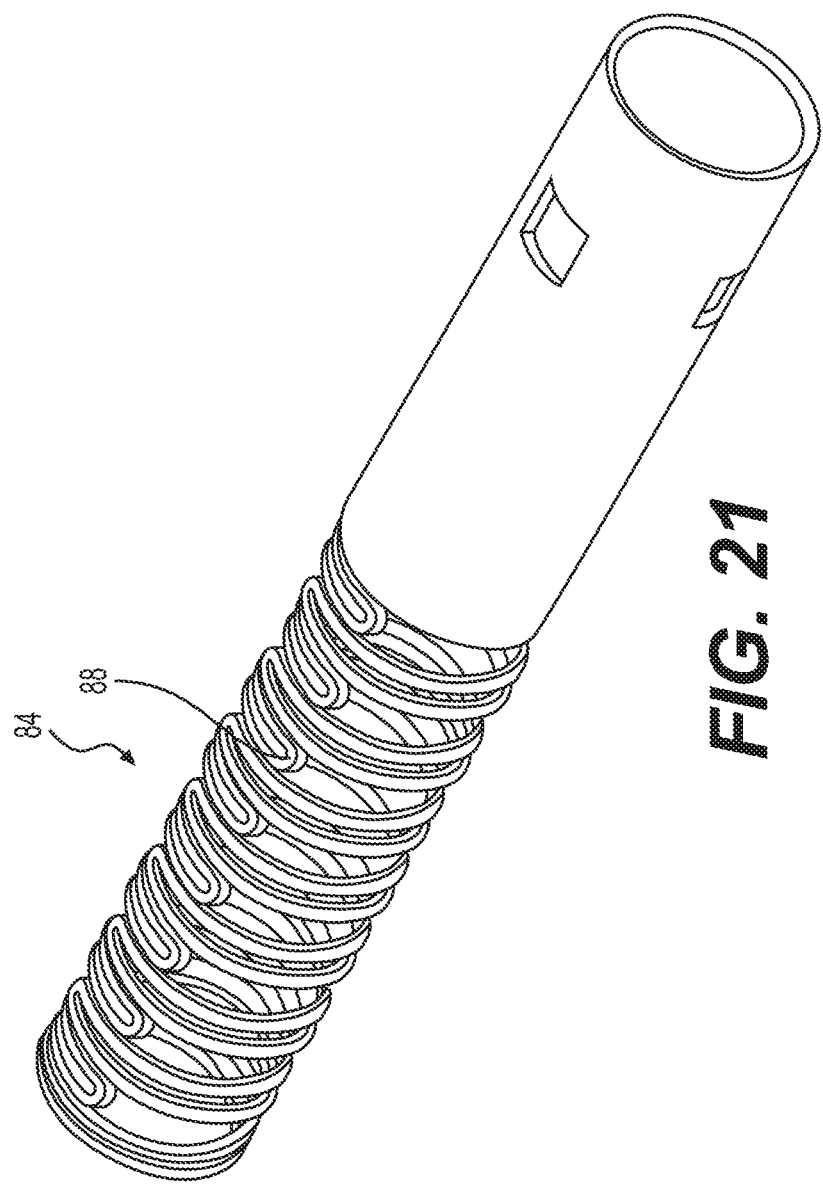
FIGS. 21-23 are perspective views of an embodiment of a stiff wall structure of a sheath having a distal stent portion progressively opening to increase its lumen diameter.
Figure 22:
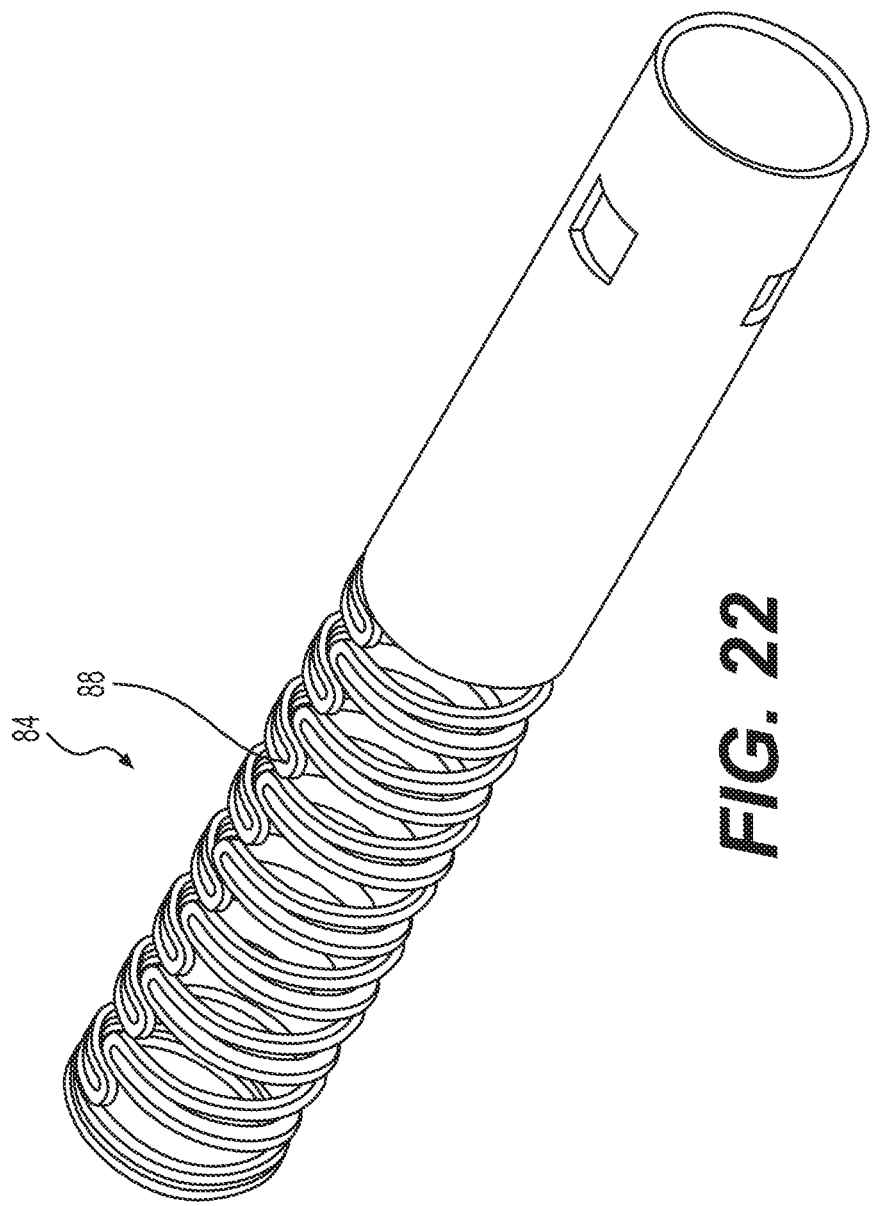
Figure 23:
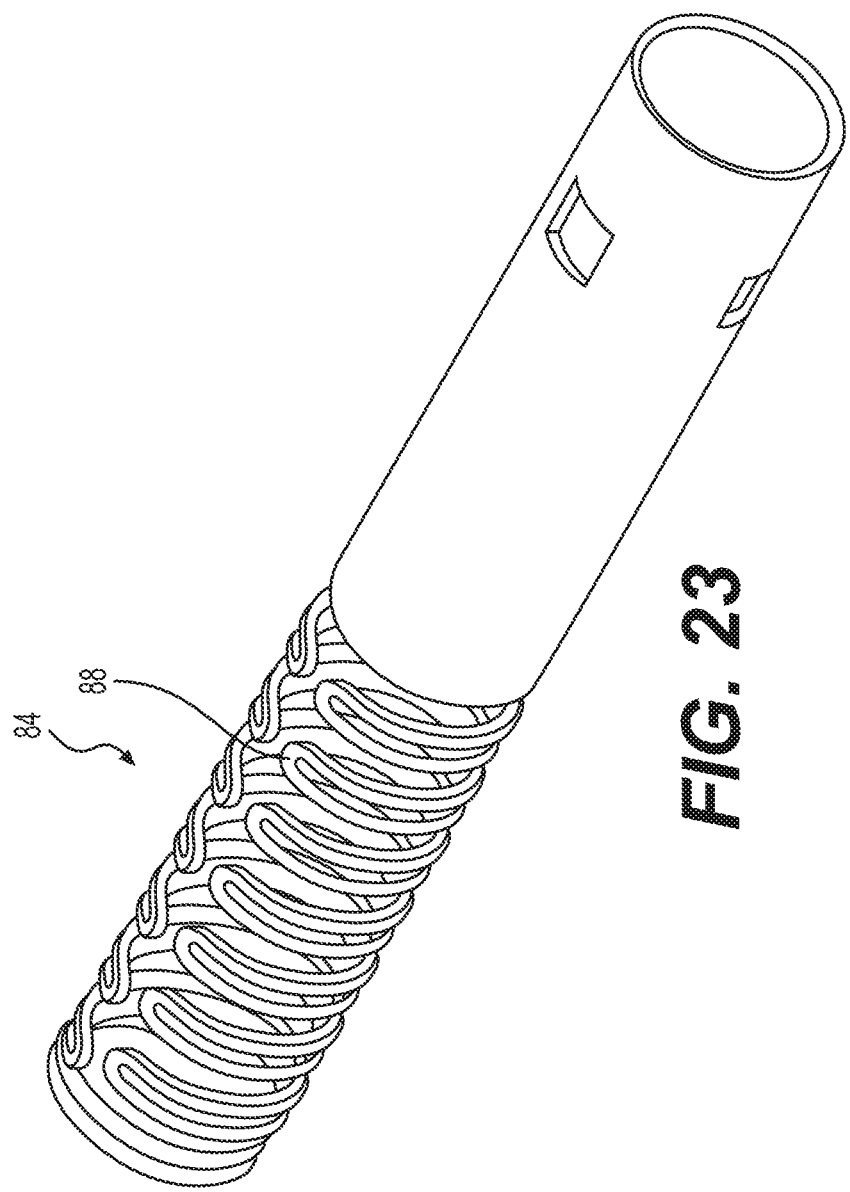

As shown in FIGS. 20-23, another embodiment of the sheath 3 can include a stent structure 84 for embedding in an elastic tubular layer. The stent 84 can include a plurality of loops 88 facing in opposite circumferential directions and that interdigitate between (FIGS. 21-23) or adjacent each other (FIG. 21) so as to be able to open up under pressure of the implant 5 passing therethrough. FIG. 20 shows an additional full circular winding 90 in between each of the loops 88 for additional stiffness. FIGS. 21, 22 and 23 show the progressive expansion of the lumen within the stent 84 as the implant 5 passes therethrough. The stent 84 can have varying lengths and in the illustrated embodiments is used for the distal end of the sheath 3. The stent 84 could also include a heat fused tip on its distal end as shown in other embodiments.

The stent 84 is a shaped frame that can be formed from a laser cut tube or by bending wire into the frame. Similar to the C-shaped stiff tubes, the stent 84 results in an off-center axial load during passage of the prosthetic implant 5. The adjacent relationship of the loops 88 and/or windings 90 provide for excellent pushing stiffness to resist buckling while still having circumferential/radial expandability. Thus, the sheath has a particularly high ratio of buckling to expansion force—allowing for good articulation with easy expansion. The stent 84 is also particularly suited for protecting delicate implants 5, like stent-mounted prosthetic heart valves. The stent 84 can be coated by polymers for hemostatic sealing and protection of the external structures of the prosthetic implant 5.

Other advantages are provided by an expandable introducer sheath for a delivery of an implant mounted on a catheter. The sheath includes an elastic outer tubular layer and an inner tubular layer having a thick wall portion integrally connected to a thin wall portion. The inner tubular layer can have a compressed condition/folded configuration wherein the thin wall portion folds onto an outer surface of the thick wall portion under urging of the elastic outer tubular layer. When the implant passes therethrough, the outer tubular layer stretches and the inner tubular layer at least partially unfolds into an expanded lumen diameter to accommodate the diameter of the implant. Once the implant passes, the outer tubular layer again urges the inner tubular layer into the folded configuration with the sheath reassuming its smaller profile. In addition to a reduced initial profile size, the integral construction of the inner tubular layer guards against the leaks and snags of prior art split-tube and uniform thickness liner combinations. The sheath may also include selectively placed longitudinal rods that mediate friction between the inner and outer tubular layers to facilitate easy expansion and collapse, thereby reducing the push force needed to advance the oversized implant through the sheath's lumen.

Figure 24:
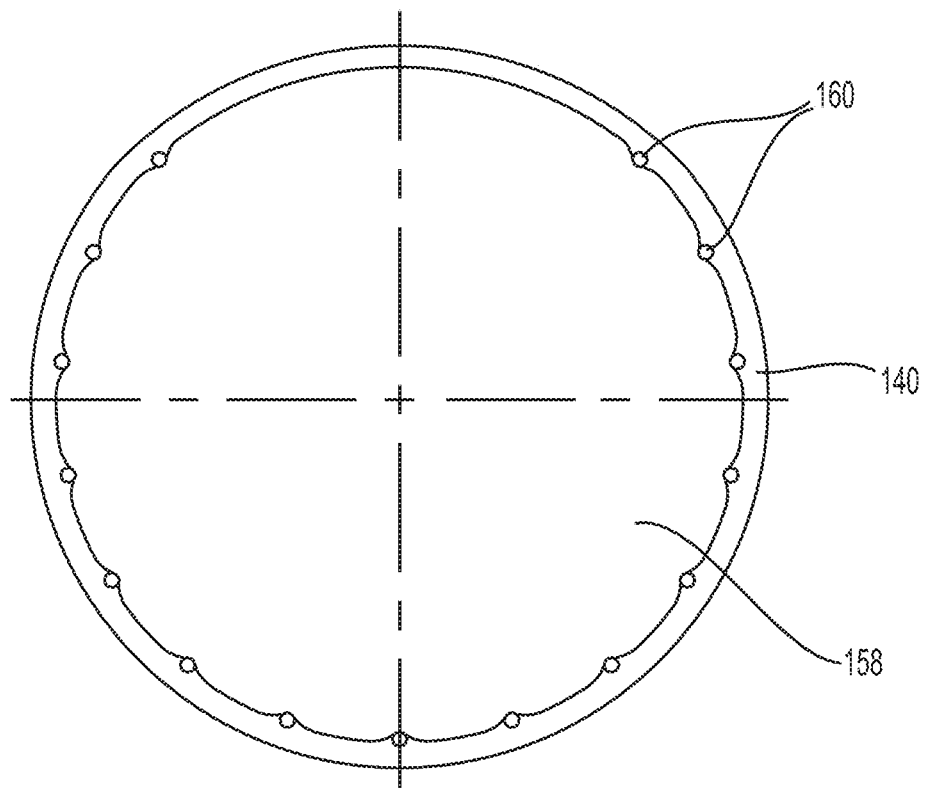
FIG. 24 is a cross sectional view of an exemplary implementation of an outer tubular layer of a sheath.
Figure 25:
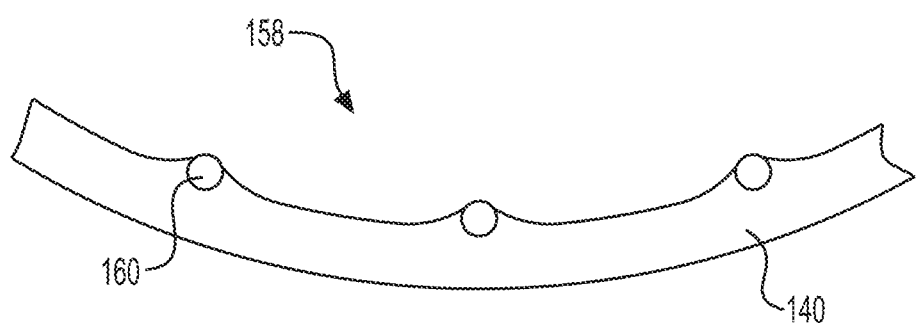
FIG. 25 is a magnified view of part of the outer tubular layer of FIG. 24, showing the cross section of longitudinal rods in greater detail.

FIG. 24 shows an implementation of the elastic outer tubular layer 140 including a plurality of longitudinal rods 160. The longitudinal rods 160 extend the length of the outer tubular layer 140 and protrude into the initial elastic lumen 158. The longitudinal rods 160 are coupled to the outer tubular layer, such as by being co-extruded and/or embedded into the elastic material of the outer tubular layer, as shown in FIG. 25. Advantageously, the longitudinal rods 160 are configured to provide a bearing surface to facilitate relative movement of the inner tubular layer 142 within the outer tubular layer 140. This is especially helpful when the inner tubular layer 142 is unfolding and returning to its originally folded shape.

The longitudinal rods 160 may be circumferentially spaced about the inside surface of the outer tubular layer 160. Although fifteen longitudinal rods 160 are shown in the cross-section of FIG. 24, any number, including a single one, of longitudinal rods may be employed. Also, the longitudinal rods 160 need not extend the entire length of the outer tubular layer 160. They may instead be applied selectively depending upon the demands of the implant, application and other circumstances. Longitudinal rods 160 may be selectively left out of an overall spacing pattern, such as in FIG. 24 where approximately 90 degrees of the inside surface of the outer tubular layer 140 is left as an unadorned surface.

Figure 26:
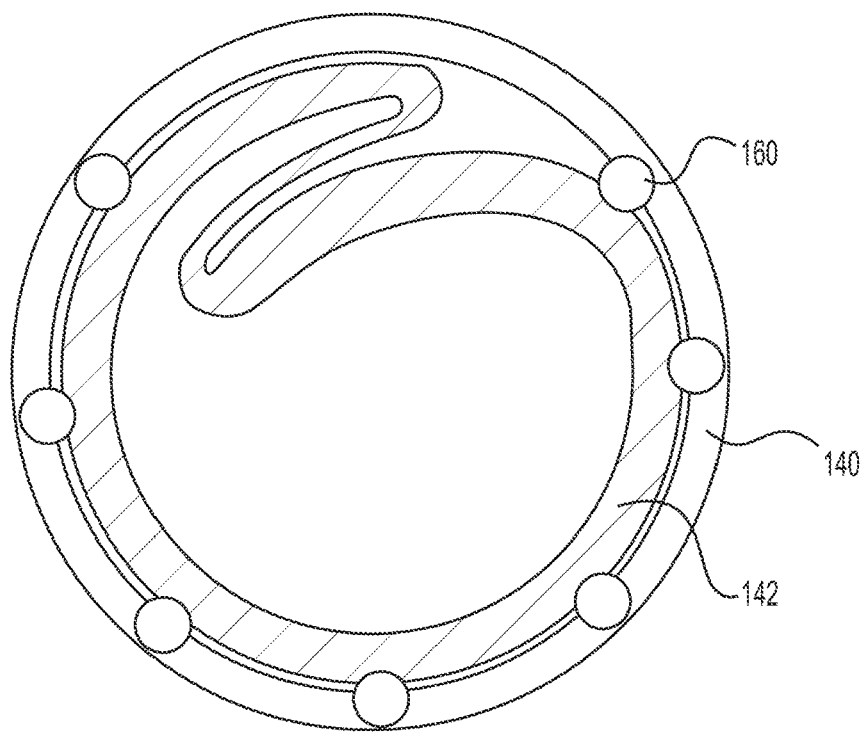
FIG. 26 shows a cross section of an exemplary embodiment including longitudinal rods embedded in the outer tubular layer and protruding into an elastic lumen.
Figure 27:
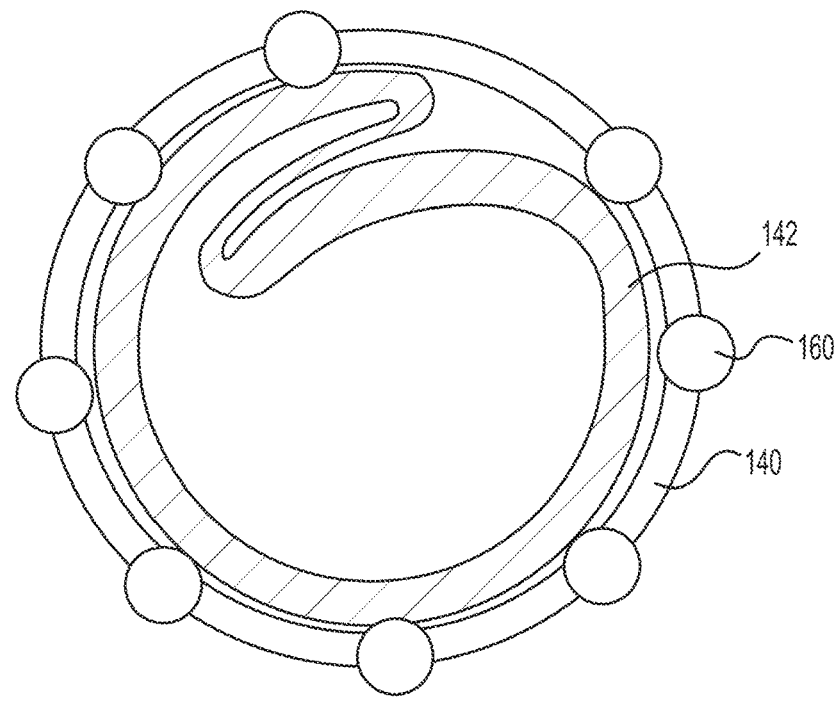
FIG. 27 shows a cross section of an exemplary embodiment including longitudinal rods embedded in the outer tubular layer and protruding into the elastic lumen and outward from the outer surface of the outer tubular layer.

As shown in FIGS. 26-29, other embodiments of the sheath may include a conventional C-shaped inner tubular layer 142 surrounded by an elastic outer tubular layer 140 employing longitudinal rods 160. (FIGS. 26-29 may also use other types of inner tubular layer 142, such as the integrally formed ones disclosed herein.) FIG. 26 shows use of seven longitudinal rods equally spaced from each other about the interior surface of the outer tubular layer 140 with the exception that a rod is missing from a portion adjacent a split in the inner tubular layer 142. This gap facilitates distraction and return of the free edges of the C-shaped inner tubular layer 142. FIG. 27 shows a similar arrangement but with the eighth longitudinal rod 60 present. But the rod is somewhat offset from the location of the free edges of the inner tubular layer 142. Furthermore, the rods of FIG. 27 protrude outward from the outer surface of the outer tubular layer 140 to lower friction between the sheath and, for example, a body lumen or an additional outer delivery sheath.

Figure 28:
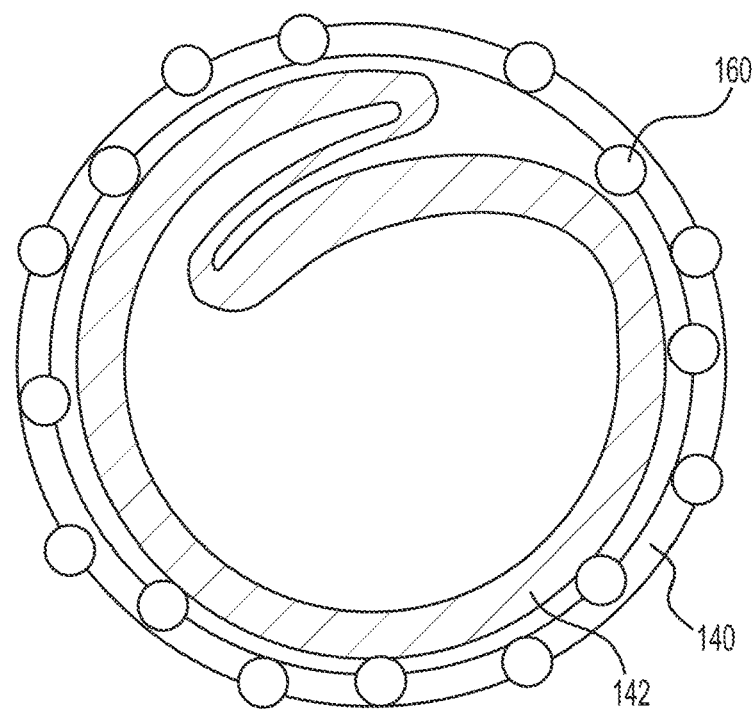
FIG. 28 shows a cross section of an exemplary embodiment including longitudinal rods embedded in the outer tubular layer, where some rods protrude into the elastic lumen and others protrude outward from the outer surface of the outer tubular layer.
Figure 29:
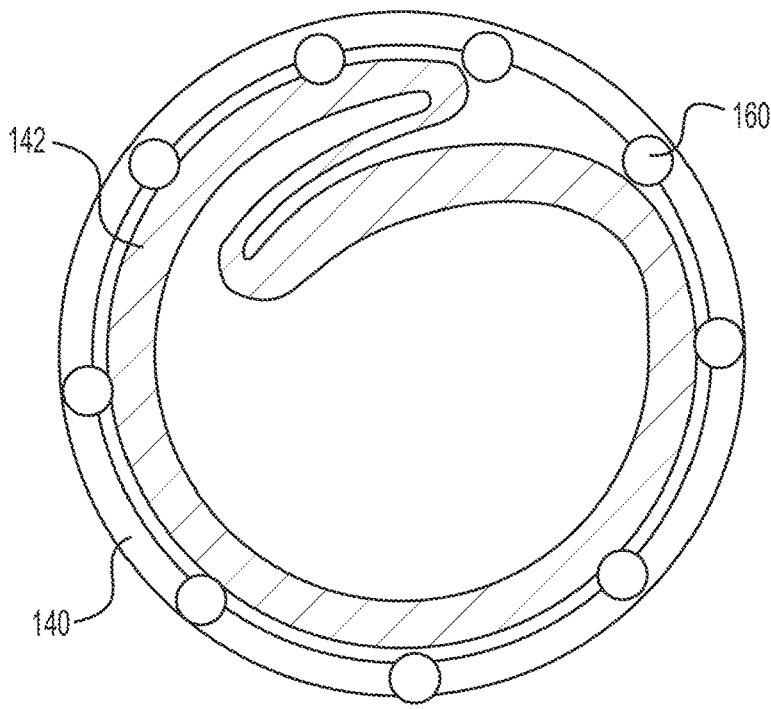
FIG. 29 shows a cross section of an exemplary embodiment including longitudinal rods embedded in the outer tubular layer and the inner tubular layer.

FIG. 28 shows another embodiment wherein rods are embedded in the outer tubular layer 140 and extend from the inside and outside surfaces thereof in alternation. This can lower friction from advancement of the sheath wherein, for example, the outer surface of the layer 140 touches a body lumen or additional outer delivery sheath. FIG. 29 shows another embodiment wherein the inner tubular layer 142 also includes a plurality of longitudinal rods 160 that facilitate, for example, easy passage of the implant 112.

The outer tubular layer 40 in the configurations of FIGS. 26-29 still can have a highly elastic, thin structure to fit over the conventional C-sheath inner tubular layer 142. As the outer tubular layer 140 is not adhered to the inner tubular layer 142, there is free movement between the sleeve and the delivery catheter. The outer tubular layer 140 is also seamless to guard against blood leakage. The sheath is stretched evenly along all segments in a radial direction—reducing the risk of tearing or fracture. And, the elastic outer tubular layer 140 will urge the C-shaped sheath back into the reduced profile configuration. During construction, the inner layer 142 is easily fitted inside the outer layer 140 without flattening or heat wrapping. Implementations may include a large number of longitudinal rods 160—even 100 or more depending upon their cross-sectional size. The longitudinal rods 160 may include microstructure patterns that further reduce friction.

Figure 30:
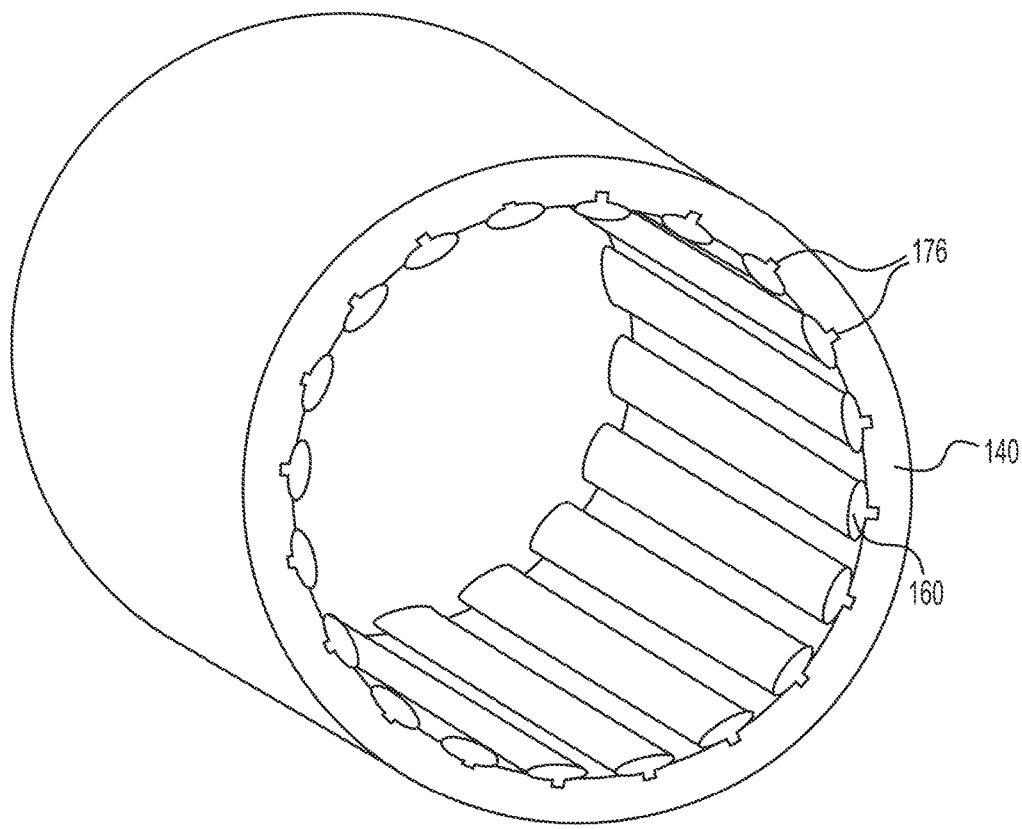
FIG. 30 shows a cross section of another exemplary embodiment including longitudinal rods embedded in the outer tubular layer and protruding into the elastic lumen.
Figure 31:
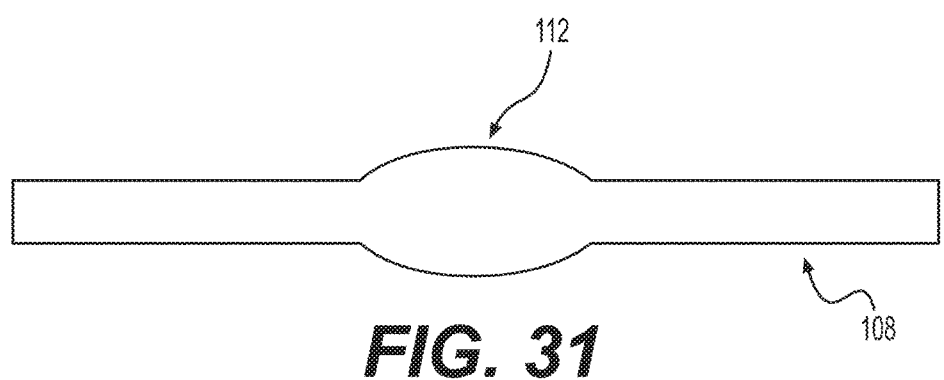
FIG. 31 shows a side view of the sheath with an implant passing therethrough.

FIGS. 30 and 31 show yet another embodiment of the sheath including a segmented outer tubular layer 140 having longitudinal rods 160 that may be employed with or without an inner tubular layer 142. As shown in FIG. 30, the outer tubular layer 140 has elongate cuts or grooves that form elongate segments 176 extending axially along inner surface. Formed or mounted along the grooves are the longitudinal rods 160. The longitudinal rods 160 are shown in FIG. 30 to have curved or arc-shaped top surfaces that reduce friction for passing implants 112. The longitudinal rods 160 are comprised of relatively high stiffness materials such as HDPE, fluropolymer and PTFE. The outer tubular layer 140 can be constructed of highly elastic materials with a low tensile set (TPE, SBR, silicone, etc.) to facilitate recovery after expansion. When used without an inner tubular layer 142, the outer tubular layer 140 can have additionally lowered expansion force—especially because the higher strength material (the rods) are not connected in the radial direction. Other variations may include changing the number and shape of the rods 160, incorporation of a tie layer or undercut/bard to strengthen the connection of the rods to the outer layer 140 and adding sections of stiff material to the outside of the outer layer for improved stiffness and pushability. A slip additive may be applied to the surfaces to increase lubricity. FIG. 31 shows the bulge in sheath 108 as the implant 112 passes therethrough.

Figure 32:
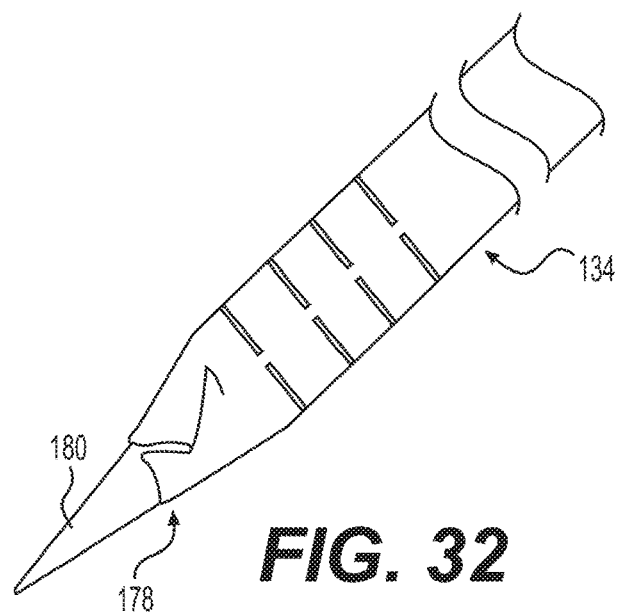
FIG. 32 shows a flared implementation of a distal portion of the sheath, where the flared portion is folded into a compressed configuration.
Figure 33:
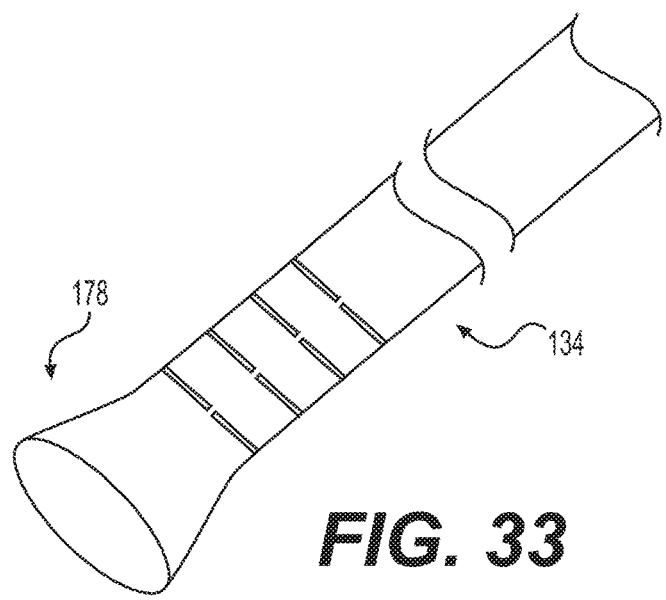
FIG. 33 shows the distal portion of FIG. 32, where the flared portion is unfolded and expanded.
Figure 34:
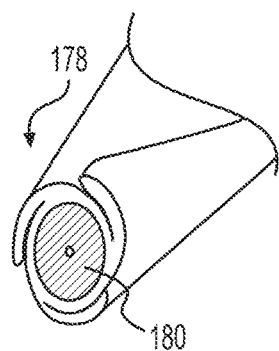
FIG. 34 shows a cross section of the distal portion of FIG. 32, where the flared portion folded into a compressed condition.

FIGS. 32-34 show another embodiment wherein a distal end of a tubular wall structure 134 can have a flared portion 178. The flared shape of the flared portion 178 helps to reduce snags or interference during retrieval experienced with conventional sheaths during retrieval of medical devices. The flared portion 178 is folded or wrapped around the tapered distal end of an introducer to maintain a low profile for advancement, as shown in FIGS. 32 and 34. The number and size of the folds may vary depending upon the size and material type of the tubular wall structure 134. For example, FIG. 34 shows three folds in a cross-sectional view. After the distal end of the sheath is in position, an introducer 180 is removed. Then, the sheath is ready to receive the delivery catheter and implant. When the implant reaches the flared portion 178 the folds then break and expand into the flared configuration, as shown in FIG. 33. The flared portion 178 remains in this flared configuration for possible retrieval of the implant.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A sheath comprising:
    an inner member comprising a central lumen extending therethrough and comprising a folded portion, a second folded portion and a third folded portion, the inner member being configured to expand to allow passage of an implant through the central lumen; and
    at least two circumferentially spaced, hard arc-segments positioned radially outward of the inner member and configured to reinforce the sheath, the hard arc-segments extending parallel to each other along a length of the sheath, each of the hard arc-segments comprising a curved inner surface, a curved outer surface, a first straight edge extending between the curved inner and outer surfaces, and a straight second edge extending between the curved inner and outer surfaces,
    wherein the folded portion of the inner member is positioned between two circumferentially spaced hard arc-segments,
    wherein the folded portion includes one or more folds,
    wherein the one or more folds comprise portions of the inner member arranged in an overlapping configuration that move to a less overlapping configuration increasing a diameter of the central lumen of the sheath to allow passage of an implant therethrough,
    wherein the third folded portion is circumferentially spaced around the inner member from the folded portion and the second folded portion, and the folded portion, second folded portion and third folded portion are equally spaced circumferentially around the inner member.

2. The sheath of claim 1, wherein each outer surface of the hard arc-segments is wider than each inner surface of the hard arc-segments.

3. The sheath of claim 1, wherein when the sheath is in an unexpanded configuration, the folded portion of the inner member is located radially inward of and is at least partially radially aligned with a circumferential spacing between the at least two hard arc-segments.

4. The sheath of claim 1, wherein the folded portion is configured to at least partially unfold during expansion of the inner member,
    wherein the at least partially unfolded portion of the folded portion is at least partially radially aligned with a circumferential spacing between the at least two hard arc-segments.

5. The sheath of claim 1, wherein when the sheath is in an unexpanded configuration, overlapping portions of the one or more folds extend longitudinally along a length of the inner member, and the overlapping portions extend generally parallel to and partially around a central longitudinal axis of the sheath.

6. The sheath of claim 1, wherein the second folded portion is circumferentially spaced around the inner member from the folded portion, the folded portion and the second folded portion located radially inward of the at least two hard arc-segments.

7. The sheath of claim 6, wherein the folded portion and the second folded portion at least partially unfold during expansion of the inner member,
wherein the at least partially unfolded portions of the folded portion and the second folded portion are at least partially radially aligned with circumferential spacings between the at least two hard arc-segments.

8. The sheath of claim 1, wherein the at least two hard arc-segments include a first, second and third outer hard arc-segment each extending along a length of the sheath, the first, second and third hard arc-segments oriented generally parallel to each other and extending in a direction generally parallel to a central longitudinal axis of the sheath,
wherein the folded portion, second folded portion and third folded portion each at least partially unfold during expansion of the inner member,
wherein the at least partially unfolded portions of the folded portion, second folded portion and the third folded portion are at least partially radially aligned with corresponding portions of circumferential spacings between the first, second and third hard arc-segments.

9. The sheath of claim 1, further comprising a distal portion of the sheath wherein the at least two hard arc-segments are embedded within a wall of an outer member that extends circumferentially around the inner member, wherein the at least two hard arc-segments and the outer member form a unitary member.

10. The sheath of claim 1, wherein the at least two hard arc-segments are attached to the wall of the inner member proximate a distal end of the sheath and proximate a proximal end of the sheath.

11. The sheath of claim 1, wherein the folded portion is located proximate a distal end of the sheath.

12. The sheath of claim 1, wherein the inner member has a starting profile configured to be smaller than the implant.

* * * * *